(12) United States Patent
Sato

(10) Patent No.: US 10,452,814 B2
(45) Date of Patent: Oct. 22, 2019

(54) ADVICE GENERATION SYSTEM, ADVICE GENERATION METHOD, AND ADVICE GENERATION DEVICE

(71) Applicant: SEIKO EPSON CORPORATION, Tokyo (JP)

(72) Inventor: Akinobu Sato, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 143 days.

(21) Appl. No.: 15/529,376

(22) PCT Filed: Nov. 16, 2015

(86) PCT No.: PCT/JP2015/005701
§ 371 (c)(1),
(2) Date: May 24, 2017

(87) PCT Pub. No.: WO2016/088309
PCT Pub. Date: Jun. 9, 2016

(65) Prior Publication Data
US 2017/0262607 A1    Sep. 14, 2017

(30) Foreign Application Priority Data

Dec. 3, 2014   (JP) .................................. 2014-244724

(51) Int. Cl.
*G06F 19/00*    (2018.01)
*G16H 50/20*    (2018.01)
(Continued)

(52) U.S. Cl.
CPC ........ *G06F 19/3418* (2013.01); *A61B 5/1118* (2013.01); *A61B 5/224* (2013.01);
(Continued)

(58) Field of Classification Search
CPC ....... A63B 1/00; A63B 2220/51; G06F 19/00; G06F 19/3418; G16H 50/20;
(Continued)

(56) References Cited

U.S. PATENT DOCUMENTS 5,954,510 A * 9/1999 Merrill .................. G09B 19/18
434/107
7,846,067 B2 * 12/2010 Hanoun ............... A63B 21/225
482/1

(Continued)

FOREIGN PATENT DOCUMENTS

JP    2002-306439 A    10/2002
JP    2007-034744 A    2/2007
(Continued)

OTHER PUBLICATIONS

Feb. 9, 2016 International Search Report issued in International Patent Application No. PCT/JP2015/005701.

*Primary Examiner* — Octavia Hollington
(74) *Attorney, Agent, or Firm* — Oliff PLC

(57) ABSTRACT

An advice generation system including: a measuring unit which measures a subject's activity status and outputs activity data based on the activity status; an achievement state acquisition unit which acquires achievement state information that is achievement state information with respect to a goal to be achieved by the subject; an amount of action calculation unit which calculates action information amount that is a cumulative amount of action taken by the subject to achieve the goal, based on the activity data acquired by the measuring unit; a motivation determination unit which determines the subject's motivation to achieve the goal based on trends of change in the achievement state information and in the amount of action information, during a period until the achievement of the goal planned by the (Continued)

| ACHIEVABILITY | HIGH |
|---|---|
| ACHIEVEMENT STATE | + |
| AMOUNT OF ACTION | + |

(a)

| ACHIEVABILITY | MIDDLE |
|---|---|
| ACHIEVEMENT STATE | 0 |
| AMOUNT OF ACTION | + |

(b)

| ACHIEVABILITY | LOW |
|---|---|
| ACHIEVEMENT STATE | − |
| AMOUNT OF ACTION | + |

(c)

subject; and an advice generation unit which generates advice for the subject based on the determination's result on the motivation.

18 Claims, 13 Drawing Sheets

(51) Int. Cl.
    *A61B 5/22*         (2006.01)
    *A61B 5/00*         (2006.01)
    *G06Q 50/22*       (2018.01)
    *A61B 5/11*         (2006.01)
    *A61B 5/024*       (2006.01)

(52) U.S. Cl.
    CPC ............ *A61B 5/486* (2013.01); *A61B 5/4866* (2013.01); *A61B 5/4869* (2013.01); *G06Q 50/22* (2013.01); *G16H 50/20* (2018.01); *A61B 5/02438* (2013.01); *A61B 2562/0219* (2013.01)

(58) Field of Classification Search
    CPC ........ A61B 5/02438; A61B 2562/0219; A61B 5/1118; A61B 5/224; A61B 5/486; A61B 5/4866; A61B 5/4869; G06Q 50/22
    USPC ..................................................... 73/379.01
    See application file for complete search history.

(56) References Cited

U.S. PATENT DOCUMENTS

| | | | |
|---|---|---|---|
| 8,568,277 | B2 * | 10/2013 | Johnson ............ H04M 1/72569 482/1 |
| 2002/0151803 | A1 | 10/2002 | Kouou |
| 2007/0239520 | A1 * | 10/2007 | Collins .................. G06Q 10/06 705/7.15 |
| 2013/0130213 | A1 * | 5/2013 | Burbank ............... A61B 5/1118 434/236 |
| 2014/0351191 | A1 * | 11/2014 | Kon ........................ G06N 5/04 706/45 |

FOREIGN PATENT DOCUMENTS

| | | |
|---|---|---|
| JP | 2009-213654 A | 9/2009 |
| JP | 2014-229212 A | 12/2014 |
| WO | 2014/188657 A1 | 11/2014 |

\* cited by examiner

| ACHIEVABILITY | HIGH |
|---|---|
| ACHIEVEMENT STATE | + |
| AMOUNT OF ACTION | + |

(a)

| ACHIEVABILITY | MIDDLE |
|---|---|
| ACHIEVEMENT STATE | 0 |
| AMOUNT OF ACTION | + |

(b)

| ACHIEVABILITY | LOW |
|---|---|
| ACHIEVEMENT STATE | − |
| AMOUNT OF ACTION | + |

| URGENCY | HIGH |
|---|---|
| ACHIEVEMENT STATE | ARBI-TRARY |
| AMOUNT OF ACTION | + |

(a)

| URGENCY | MIDDLE |
|---|---|
| ACHIEVEMENT STATE | − |
| AMOUNT OF ACTION | 0 |

(b)

| URGENCY | LOW |
|---|---|
| ACHIEVEMENT STATE | + |
| AMOUNT OF ACTION | 0 |

| DEGREE OF DIFFICULTY \ OBJECTIVE | OBJECTIVE A WEIGHT LOSS | OBJECTIVE B FULL MARATHON | OBJECTIVE C HALF MARATHON |
|---|---|---|---|
| LEVEL 1 | GROUP A1 | GROUP B1 | GROUP C1 |
| LEVEL 2 | GROUP A2 | GROUP B2 | GROUP C2 |
| LEVEL 3 | GROUP A3 | GROUP B3 | GROUP C3 |
| LEVEL 4 | GROUP A4 | GROUP B4 | GROUP C4 |
| LEVEL 5 | GROUP A5 | GROUP B5 | GROUP C5 |

(b) 213

| CURRENT STATE \ TARGET WEIGHT LOSS | 30Kg | 20Kg | 10Kg |
|---|---|---|---|
| 100Kg | LEVEL 3 | LEVEL 2 | LEVEL 1 |
| 90Kg | LEVEL 4 | LEVEL 3 | LEVEL 2 |
| 80Kg | LEVEL 5 | LEVEL 4 | LEVEL 3 |

(c) 215

| CURRENT STATE \ TARGET | 2h30m | 3h | 3h30m | 4h | 4h30m |
|---|---|---|---|---|---|
| 3h | LEVEL 5 | | | | |
| 3h30m | | LEVEL 4 | | | |
| 4h | | | LEVEL 3 | | |
| 4h30m | | | | LEVEL 2 | |
| 5h | | | | | LEVEL 1 |

(d) 217

| CURRENT STATE \ TARGET | 1h15m | 1h30m | 1h45m | 2h | 2h15m |
|---|---|---|---|---|---|
| 1h30m | LEVEL 5 | | | | |
| 1h45m | | LEVEL 4 | | | |
| 2h | | | LEVEL 3 | | |
| 2h15m | | | | LEVEL 2 | |
| 2h30m | | | | | LEVEL 1 |

FIG. 12

ADVICE GENERATION SYSTEM, ADVICE GENERATION METHOD, AND ADVICE GENERATION DEVICE

CROSS-REFERENCES TO RELATED APPLICATIONS

This application claims priority to Japanese Patent Application No. 2014-244724 filed Dec. 3, 2014, the entirety of which is herein incorporated by reference.

TECHNICAL FIELD

The present invention relates to an advice generation system, an advice generation method, and an advice generation device involved in exercise coaching and health coaching.

BACKGROUND ART

Traditionally, a system for providing advice to a subject who is a person to be coached, in order to achieve a goal set in health coaching or exercise coaching, is known. PTL 1 discloses a device which provides information to give a motivation to continue training such as walking or jogging.

CITATION LIST

Patent Literature

PTL 1: JP-A-2009-213654

SUMMARY OF INVENTION

Technical Problem

However, the device disclosed in PTL 1 is far from providing information which enables or motivates the subject to maintain a highly motivated state. Specifically, the device according to PTL 1 provides information to encourage the subject in the case where the amount of training of the subject is less than the planned amount of training. The information provided based on such a comparison of the statuses of the amounts of training can lower the motivation of the subject. For example, if the goal is too high for the athletic ability of the subject, the subject needs training over a long period. During that period, advice to encourage the subject is provided. Even if the subject continues training, with the advice provided repeatedly, the subject becomes unsure about whether he/she can achieve the goal, and therefore the level of motivation drops.

One of the theoretical models developed from the expectancy theory (1964) of Victor Vroom, who proposed a mechanism of motivation, is a theoretical model that motivation involves the three elements of attraction, achievability, and urgency of the goal, and that the level of motivation corresponds to the multiplication of these elements (see "Business Leaders' Training Material", Motivation Mechanism, http://blog.nikkeibp.co.jp/nb/academic/university/pdf/soukadaigaku_inuzukakenkyu6.pdf). According to this theoretical model, in order to maintain the high level of motivation held at the time of setting a goal, psychological states of achievability and urgency, which can easily change after the start of training, are important elements. In the above example, the level of motivation drops because the element of achievability decreases, from among the subject's feelings.

In this way, with the information provided simply based on the comparison between the states of the amounts of training, the level of motivation of the subject may drop and therefore advice corresponding to the conditions of motivation of the subject needs to be provided.

Solution to Problem

In order to solve at least a part of the foregoing problem, the invention can be implemented in the following forms or application examples.

Application Example 1

An advice generation system according to this application example is an advice generation system which generates advice for achieving a goal. The system includes: a measuring unit which measures an activity status of a subject and outputs activity data based on the activity status; an achievement state acquisition unit which acquires achievement state information that is information of an achievement state with respect to a goal of the subject; an amount of action calculation unit which calculates amount of action information that is a cumulative amount of action taken by the subject based on the activity data acquired by the measuring unit; a motivation determination unit which determines motivation of the subject to achieve the goal based on the achievement state information and the amount of action information; and an advice generation unit which generates advice for the subject based on a result of the determination on the motivation.

According to this application example, the motivation of the subject is determined based on the achievement state information and the amount of action information of the subject acting to achieve the goal. Advice is generated based on the result of the determination on the motivation. Advice reflecting the state of motivation of the subject can be generated.

Therefore, advice corresponding to the conditions of motivation of the subject can be provided to the subject.

Application Example 2

The motivation determination unit may determine the motivation based on a trend of change in the achievement information and a trend of change in the amount of action information.

According to this application example, the motivation of the subject acting to achieve the goal can be accurately determined.

Application Example 3

The achievement state information and the amount of action information may be acquired every predetermined period.

According to this application example, the information of the achievement state and the amount of action of the subject can be acquired as needed.

Application Example 4

The motivation determination unit may determine levels of achievability of the subject and urgency of the subject.

According to this application example, the state of motivation of the subject can be determined by determining the achievability and the level of urgency of the subject.

Application Example 5

The motivation determination unit may determine that it is a first level of the achievability if the trend of change in the amount of action information is an ascending trend and the trend of change in the achievement state information is a trend of change that is approaching a goal achievement state.

According to this application example, levels of achievability corresponding to various states can be determined by referring to the first level of achievability, which is the state where the amount of action information of the subject increases and the achievement state information is approaching the goal achievement.

Application Example 6

The motivation determination unit may determine that the achievability is a second level of achievability that is lower than the first level of achievability, if the trend of change in the amount of action information is an ascending trend and the trend of change in the achievement state information is within a predetermined range of trend of change.

According to this application example, achievability that is lower than the first level of achievability can be determined.

Application Example 7

The motivation determination unit may determine that the achievability is a third level of achievability that is lower than the second level of achievability, if the trend of change in the amount of action information is an ascending trend and the trend of change in the achievement state information is a trend of change that is far from a goal achievement state.

According to this application example, achievability that is lower than the second level of achievability can be determined.

Application Example 8

The motivation determination unit may determine that it is a first level of urgency if the trend of change in the amount of action information is an ascending trend.

According to this application example, levels of urgency corresponding to various states can be determined by referring to the first level of urgency, which is the state where the amount of action information of the subject increases.

Application Example 9

The motivation determination unit may determine that the urgency is a second level of urgency that is lower than the first level of urgency, if the trend of change in the amount of action information is within a predetermined range of trend of change and the trend of change in the achievement state information is a trend of change that is far from a goal achievement state.

According to this application example, urgency that is lower than the first level of urgency can be determined.

Application Example 10

The motivation determination unit may determine that the urgency is a third level of urgency that is lower than the second level of urgency, if the trend of change in the amount of action information is within a predetermined range of trend of change and the trend of change in the achievement state information is a trend of change that is approaching a goal achievement state.

According to this application example, urgency that is lower than the second level of urgency can be determined.

Application Example 11

The activity status of the subject may include a pulse rate of the subject and acceleration information based on a body movement of the subject, and the activity data may include at least one of pulse data calculated based on the pulse rate and acceleration data calculated based on the acceleration information.

According to this application example, the action of the subject can be accurately grasped based on the pulse rate and the acceleration information of the subject.

Application Example 12

The amount of action calculation unit may calculate exercise intensity using at least one of the pulse data and the acceleration data of the subject, and calculate the amount of action based on the exercise intensity and a duration of the exercise intensity.

According to this application example, the amount of action can be accurately calculated with respect to various actions with different exercise intensities.

Application Example 13

The amount of action calculation unit may calculate calories burned, using at least one of the pulse data and the acceleration data of the subject, and calculate the amount of action based on the calories burned that are accumulated.

According to this application example, amounts of action corresponding to various actions can be accurately calculated by calculating and accumulating the calories burned generated by the action of the subject.

Application Example 14

The achievement state information may include at least one of weight of the subject, a time taken for the subject to run a predetermined distance, a distance which the subject can run, and a physical strength indicator of the subject.

According to this application example, the state until the goal of the subject is achieved can be acquired based on the achievement state information and used for the determination of motivation.

Application Example 15

The physical strength indicator may be a maximum oxygen uptake of the subject.

According to this application example, the system is effective in the case where the objective of the subject is an action relating to improvement in cardiopulmonary function.

Application Example 16

The advice generation system may further include: a storage unit which acquires at least a goal, a period until the goal is achieved, and the activity data, of a plurality of subjects, and stores the achievement state information and the amount of action information acquired or calculated for each of the subjects; and a grouping unit which groups the plurality of subjects based on the achievement state information and the amount of action information of the plurality of subjects stored in the storage unit. The advice generation unit may generate advice for the subject, referring to the achievement state information and the amount of action information of the subject and another subject in the same group as the subject.

According to this application example, advice to maintain the motivation of the subject at a higher level can be generated by referring to the information of another subject in the same group.

Application Example 17

The advice generation system may further include a predetermined period change unit which changes an interval of the predetermined period based on a result of the determination of motivation.

According to this application example, a drop in the motivation of the subject can be restrained by changing the interval of the predetermined period.

Application Example 18

The predetermined period change unit may change the interval of the predetermined period to be longer if it is determined that the motivation is the first level of achievability.

According to this application example, in the case where the interval of the predetermined period is changed to be shorter, the interval of the predetermined period can be returned to the original interval if the state of achievability becomes higher.

Application Example 19

The predetermined period change unit may change the interval of the predetermined period to be shorter if it is determined that the motivation is the second level of achievability or the third level of achievability.

According to this application example, a reduction in the state of achievability of the subject can be restrained and improved by shortening the interval of the predetermined period.

Application Example 20

An advice generation method for generating advice to achieve a goal includes: measuring an activity status of a subject and outputting activity data based on the activity status; acquiring achievement state information that is information of an achievement state with respect to a goal of the subject; calculating amount of action information that is a cumulative amount of action taken by the subject based on the activity data acquired by the measuring; determining motivation of the subject to achieve the goal based on the achievement state information and the amount of action information; and generating advice for the subject based on a result of the determination on the motivation.

According to this application example, the motivation of the subject is determined based on the achievement state information and the amount of action information of the subject acting to achieve the goal. Advice is generated based on the result of the determination on the motivation. Advice reflecting the state of motivation of the subject can be generated. Therefore, advice corresponding to the conditions of motivation of the subject can be provided to the subject.

Application Example 21

An advice generation device for generating advice to achieve a goal includes: a measuring unit which measures an activity status of a subject and outputs activity data based on the activity status; an achievement state acquisition unit which acquires achievement state information that is information of an achievement state with respect to a goal of the subject; an amount of action calculation unit which calculates amount of action information that is a cumulative amount of action taken by the subject based on the activity data acquired by the measuring unit; a motivation determination unit which determines motivation of the subject to achieve the goal based on the achievement state information and the amount of action information; and an advice generation unit which generates advice for the subject based on a result of the determination on the motivation.

According to this application example, the motivation of the subject is determined based on the achievement state information and the amount of action information of the subject acting to achieve the goal. Advice is generated based on the result of the determination on the motivation. Advice reflecting the state of motivation of the subject can be generated. Therefore, advice corresponding to the conditions of motivation of the subject can be provided to the subject.

BRIEF DESCRIPTION OF DRAWINGS

FIG. 1 is a view explaining the result of determination on achievability.

FIG. 2 is a view explaining the result of determination on urgency.

FIG. 12 is a view explaining an example of a grouping table.

DESCRIPTION OF EMBODIMENTS

Figure 3:
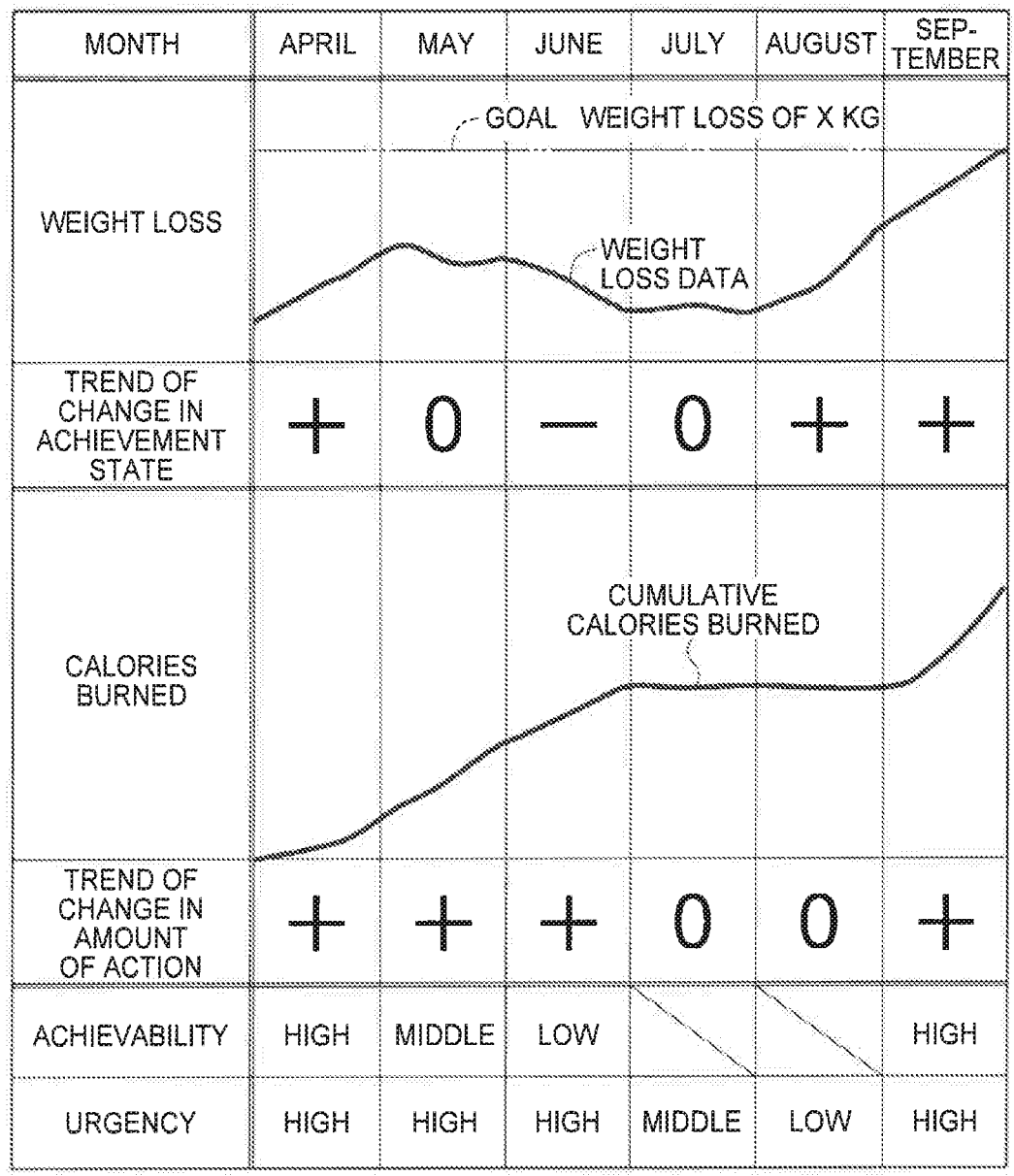
FIG. 3 is a view showing an example of the result of determination by a motivation determination method.

Hereinafter, embodiments of the invention will be described. The embodiments described below should not unduly limit the contents of the invention described in the claims. Also, not all the configurations described in the embodiments are essential components.

Embodiment 1

(Principle)

An advice generation system according to this embodiment provides advice to maintain a high level of motivation, to a subject acting to achieve a goal for the purpose of health improvement and enhancement of athletic ability. Motivation expresses the psychological state to continue an action toward the achievement of the goal during the time until the achievement of the goal from the point when the subject starts the action to achieve the goal. If the motivation of the subject is high, the action is continued smoothly until the achievement of the goal. If the motivation is low, the situation where the action can be interrupted may occur. The advice generation system generates and provides advice corresponding to the state of the motivation of the subject, at a proper timing and with a proper content, so as to guide the subject toward the prevention of a drop in the motivation of the subject and improvement of the motivation if the motivation of the subject drops, and to maintain the state of high motivation if the motivation of the subject is high.

The motivation is expressed by the following equation (1) in the theoretical model developed from the expectancy theory.

$$\text{Motivation} = \text{attraction of goal} \times \text{achievability} \times \text{urgency} \quad (1)$$

The motivation is the multiplication of the three elements expressing psychological states of the subject, that is, the attraction of the goal, its achievability, and its urgency.

The attraction of the goal represents a psychological state indicating whether it is a goal which the subject him/herself wants to achieve. If the goal is attractive to the subject, the feeling of wanting to do it is cultivated and the motivation becomes higher. On the contrary, if the subject no longer finds the goal attractive, the motivation drops.

The achievability is a psychological state indicating whether subject is likely to be able to achieve the goal. If the subject is likely to be able to achieve the goal, the feeling that the goal is almost within reach is cultivated and the motivation becomes higher. On the contrary, if the subject finds it hard to achieve the goal, the motivation drops.

The urgency is a psychological state indicating the level of anxiety and tension in the case where the subject cannot achieve the goal. If the disadvantage in the case where the subject cannot achieve the goal is great, the feeling of having to do it is cultivated and the motivation becomes higher. On the contrary, if the disadvantage is small, the motivation drops.

Since the motivation is the multiplication of the above three elements, the motivation is increased by maintaining the psychological state of each element at a high level, and if the psychological state of one of the elements is low, the motivation drops and the subject finds it difficult to continue the action to achieve the goal.

Since such three elements are the subjective psychological states of the subject, information thereof can be gathered directly from the subject and quantified by questions and answers or by questionnaires. However, there are cases where accurate information cannot be obtained from questions and answers or from responses to questionnaires, due to various factors particular to the subject. Particularly, at the point when the subjects starts an action to achieve the goal, the subject is in a calm state and responses to a relatively accurate psychological state can be obtained, whereas after the lapse of some time, emotions and the like such as emotional attachment to the action status and achievement status up to that point are taken into consideration, making it difficult to obtain responses to an accurate psychological state of the subject. For example, in the response about the achievability of whether "the subject can achieve the goal", if the subject has a very strong will to achieve the goal even if the user is already taking a course of events that the subject cannot achieve the goal, it is conceivable that the subject gives a response that "he/she can achieve the goal". Also, in the response about the urgency, it is conceivable that the subject pretends to have a sense of urgency in order to show that he/she is willing to do it, and therefore ends up giving a response that "it is very urgent".

Of the three elements, the element of attraction of the goal is an element reflecting emotions, attachment, willingness and the like of the subject and therefore may be quantified in the form of questions and answers or responses to questionnaires.

In this embodiment, the explanation of the element of attraction of the goal is omitted hereinafter. It is assumed that the element of attraction of the goal is constantly in the state of being maintained at a high level by direct coaching by an instructor based on the questions and answers or questionnaires.

In the motivation determination method in the embodiment, the psychological states based on the elements of achievability and urgency of the subject acting to achieve the goal are quantified based on the goal achievement state and the information of the amount of action of the subject, so as not to include the influence of emotions, attachment and the like of the subject.

(Principle of Motivation Determination Method)

In the motivation determination method, the psychological states based on the elements of achievability and urgency are quantified, utilizing the achievement state information and the amount of action information of the subject.

The achievement state information is information obtained by measuring the achievement state shifting until the subject achieves the goal. For example, if the goal of the subject is weight loss of 5 kg, the weight lost by the subject that is measured is the achievement state information.

The amount of action information is information of the amount of action taken by the subject until the achievement of the goal. For example, if the subject has a goal of 5 kg weight loss and carries out cardio exercise corresponding to 300 kcal every day, calories burned found by multiplying 300 kcal by the number of days elapsed is the amount of action information.

In the advice generation system, a measuring device which measures the activity status of the subject is included and the amount of action information is calculated from the measured activity status. Details of the measuring device will be described later.

In the motivation determination method, trends of change in the achievement state information and the amount of action information are calculated.

The trend of change in the achievement state information is a positive (+) trend (hereinafter referred to as a + trend)

if the measured value of the achievement state is approaching a goal as a final goal during a predetermined period (for example, one month), from the start of the period to the end of the period, and a negative (−) trend (hereinafter referred to as a − trend) if the measured value is getting far from the goal. If no change is observed, that is, if the measured value is neither approaching the goal nor getting far from the goal, there is no change and the trend is defined as a (0) trend (hereinafter referred to as 0 trend.

The trend of change in the amount of action information is a + trend if the cumulative amount of action is increasing during a predetermined period, from the start of the period to the end of the period, and a 0 trend if no change is observed in the cumulative amount of action. If the trend of change in the amount of action is a 0 trend, it means that the subject has not taken any action toward the achievement of the goal.

In the determination on the 0 trend with respect to the trend of change in the achievement state information and the trend of change in the amount of action information, the trend may be determined as the 0 trend if it is within a predetermined range of trend of change. In that case, it is a + trend if the value is increasing beyond the predetermined range of trend of change, and a − trend if the value is getting far from the goal beyond the predetermined range of trend of change.

FIG. 1 is a view explaining the result of determination on the achievability. FIG. 2 is a view explaining the result of determination on the urgency.

FIG. 1(a) is a view explaining conditions under which the result of determination on the achievability is "high". If both the achievement state and the amount of action are in the + trend, it means that the achievability is high. Since the effect that the achievement state is approaching the goal is observed as the result of a sufficient action (exercise) carried out by the subject, the subject is in a psychological state that the he/she can achieve (likely to achieve) the goal and the achievability of the subject is high.

The achievability on which the result of determination is "high" corresponds to the first level of achievability.

FIG. 1(b) is a view explaining conditions under which the result of determination on the achievability is "middle". If the achievement state is in the 0 trend and the amount of action is in the + trend, it means that the achievability is at a middle level. Since no change is observed in the achievement state despite the sufficient action taken by the subject, the subject is in the state of waiting for the trend of change in the achievement state in the future, while continuing the action. In this case, the achievability of the subject is lower than the result of determination of "high".

The achievability on which the result of determination is "middle" corresponds to the second level of achievability.

FIG. 1(c) is a view explaining conditions under which the result of determination on the achievability is "low". If the achievement state is in the − trend and the amount of action is in the + trend, it means that the achievability is low. Despite the sufficient action taken by the subject, it is counterproductive since the achievement state is getting far from the goal. In such a state, the subject falls in a psychological state that he/she cannot achieve the goal even if he/she continues the action that is now underway, and therefore the achievability of the subject is significantly low. In this case, the achievability of the subject is lower than the result of determination of "middle".

The achievability on which the result of determination is "low" corresponds to the third level of achievability.

FIG. 2(a) is a view explaining conditions under which the result of determination on the urgency is "high". If the achievement state is in an arbitrary trend and the amount of action is in the + trend, it means that the urgency is high. The subject is in the state of continuing the action toward the achievement of the goal no matter what the achievement state is, and therefore the urgency of the subject is high.

The urgency on which the result of determination is "high" corresponds to the first level of urgency.

FIG. 2(b) is a view explaining conditions under which the result of determination on the urgency is "middle". If the achievement state is in the − trend and no change is observed in the amount of action, it means that the urgency is at a middle level. Since the subject is not acting toward the achievement of the goal even though the achievement state is far from the goal, the subject lacks psychological states such as anxiety and tension in the case of being unable to achieve the goal and therefore the urgency of the subject is lower than the result of determination of "high".

The urgency on which the result determination is "middle" corresponds to the second level of urgency.

FIG. 2(c) is a view explaining conditions under which the result of determination on the urgency is "low". If the achievement state is in the + trend and no change is observed in the amount of action, it means that the urgency is low. Since the subject is approaching the state of achieving the goal even though the subject is not executing any action toward the achievement of the goal, the subject is less likely to fall in psychological states such as anxiety and tension in the case of being unable to achieve the goal. Since the urgency is lacking because the subject is approaching the achievement of the goal even without taking action toward the achievement of the goal, the urgency of the subject is lower than the result of determination of "middle".

The urgency on which the result of determination is "low" corresponds to the third level of urgency.

FIG. 3 is a view showing an example of the result of determination by the motivation determination method. FIG. 3 explains the status of the results of determination on the achievability and urgency determined by the advice generation system in a process in which a subject setting a goal of X (kg) body weight loss achieves the goal.

The advice generation system acquires, from the subject, information such as the state of the subject at the time of setting the goal and at the time of achieving the goal, the period until the achievement of the goal, the content of the action to achieve the goal, the amount of action taken until the achievement of the goal, and the regular check period.

In this example, the time of setting the goal is April 1. The state of the subject at the time of setting the goal is the body weight of the subject on April 1. The state at the time of achieving the goal is X (kg) weight loss. The period until the achievement of the goal is six months from April 1 to September 30. Also, the content of the action to achieve the goal is cardio exercise. The indicator of the amount of action is calories burned at the time of the cardio exercise. The regular check period is one month and the achievability and urgency, which are elements of motivation, are determined at the end of each month. The amount of action until the achievement of the goal is calories burned found by multiplying 7000 kcal by X (kg) in the case of the condition that 7000 kcal need to be burned to achieve weight loss of 1 kg, for example. The cardio exercise may be jogging, walking or the like. A measuring device 10 (FIG. 4), described later, is mounted on the subject, and calories burned are calculated by the measuring device 10.

In the row of "weight loss" shown on an upper stage in the FIG. 3, a graph of weight loss data is shown. The graph of weight loss data is a graph on which the weight lost is plotted in time series. The weight loss progresses from the beginning of April to the beginning of May and then stagnates in May. In June, the weight loss regresses (the weight is gained). Subsequently, the weight loss stagnates in July and then progresses from the beginning of August to the end of September, achieving the goal of X (kg) weight loss.

In the row of "trend of change in achievement state", the trend of change in the achievement state for each month is indicated in the form of "+", "−", or "0". These represent the + trend, − trend, and 0 trend in this order. In the trend of change in the achievement state of FIG. 3, since the weight loss progresses from the beginning to the end of April, it is the + trend. In May, the difference between the beginning and end of May is small and therefore it is the 0 trend. In June, the weight loss regresses from the beginning to the end of June and therefore it is the − trend. Similarly, it is the 0 trend in July and the + trend in August and September.

In the row of "calories burned", a graph of cumulative calories burned is shown. The graph of cumulative calories burned is a graph on which the cumulative amount of calories burned that is calculated is plotted in time series. The calories burned are accumulated from the beginning of April to the end of June. The calories burned stagnate in July and August. The calories burned are accumulated and increased in September.

In the row of "trend of change in amount of action" the trend of change in the amount of action for each month is indicated in the form of "+", "−", or "0". These represent the + trend, − trend, and 0 trend in this order. Specifically, in April, May, and June, the cumulative calories burned increase from the beginning to the end of the month and therefore it is the + trend. In July and August, the amount of increase in the calories burned is small from the beginning to the end of the month and therefore it is the 0 trend. In September, the cumulative calories burned increase from the beginning to the end and therefore it is the + trend.

In the rows of "achievability" and "urgency" at the bottom in FIG. 3, the results of determination of the "achievability and "urgency" are shown. From the combination pattern of the trend of change in the achievement state and the trend of change in the amount of action shown in FIG. 1 and FIG. 2, the results of determination on the achievability and urgency are calculated for each month. The result of determination on the achievability is indicated by a slant line for July and August. Since no pattern is defined as a determination pattern for determining the achievability in the case where the trend of change in the amount of action is the 0 trend, a slant line is placed, indicating that the determination is unavailable.

In this way, in the motivation determination method, the psychological states of achievability and urgency are calculated based on the result of measuring the state of the subject. Thus, quantification is realized without being based on emotions and thoughts of the subject.

The results of determination on the achievability and urgency are expressed in stages such as "high", "middle", and "low". However, these stages may be expressed in a numerical form. For example, using the numerical values of 10 to 0, numerical expressions may be given, such as 10 for "high", 5 for "middle", and 1 for "low". Also, while the trend of change in the achievement state and the trend of change in the amount of action are explained in the form of the + trend, − trend, or 0 trend, each trend may be further divided into multiple stages. For example, multiple stages may be set from the case where the achievement state is significantly high (the gradient of the + trend is large) to the case where the achievement state is close to stagnation, depending on the degree of gradient of the trend of change in the achievement state. As the trend of change in the achievement state and the trend of change in the amount of action include multiple stages in this way, results of determination in multiple stages are calculated with respect to the achievability and urgency determined based on the combination thereof.

The advice generation system can generate advice for the subject in order to maintain motivation at a high level for each type of the results of determination on the achievability and urgency calculated by the motivation determination method.

Hereinafter, the configuration of such an advice generation system will be described.

(Advice Generation System)

(Configuration of Advice Generation System)

Figure 4:
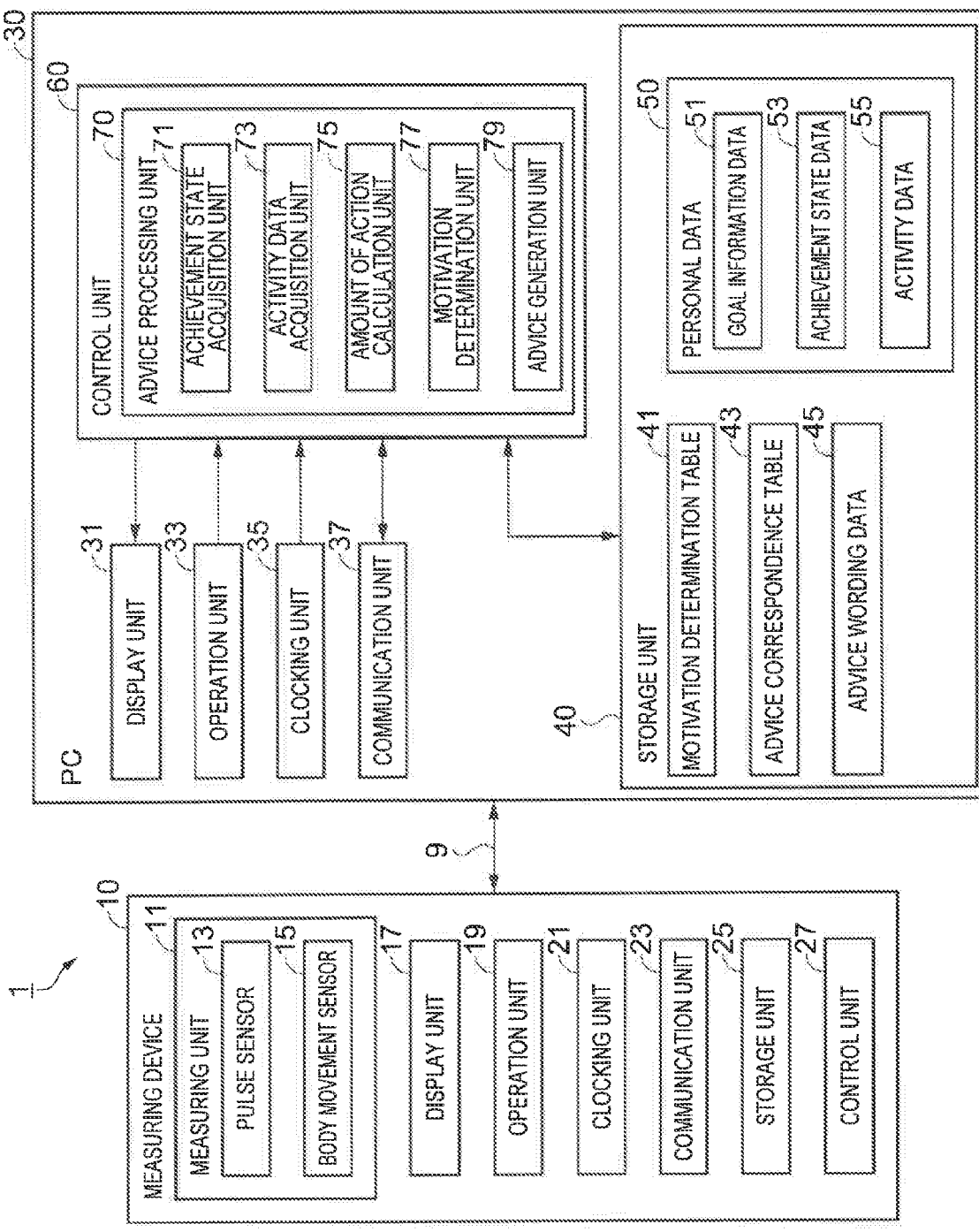
FIG. 4 is a block diagram showing a schematic configuration of an advice generation system.

FIG. 4 is a block diagram showing a schematic configuration of an advice generation system 1.

The advice generation system 1 is made of a measuring device 10 and a PC 30 or the like.

The measuring device 10 is a small portable device mounted on the wrist or the like of the subject and measures the activity status by detecting the pulse rate, body movement and the like of the subject during an activity. The activity status measured by the measuring device 10 is transmitted as activity data to the PC 30 via wireless communication 9 such as short-range wireless. The PC 30 is a common personal computer, smartphone or the like, where software which psychologically supports the subject acting to achieve a goal that is set for the purpose of health improvement or enhancement of athletic ability is executed. As the software is executed, the PC 30 analyzes the state of the motivation of the subject with the use of the received activity data and generates advice to maintain or improve the motivation.

(Configuration of Measuring Device 10)

The measuring device 10 is made up of a measuring unit 11, a display unit 17, an operation unit 19, a clocking unit 21, a communication unit 23, a storage unit 25, and a control unit 27 or the like.

The measuring unit 11 has the function of detecting the pulse rate of the subject and acceleration information or the like based on body movements of the subject, and outputting such information as activity data, and is made up of a pulse sensor 13 and a body movement sensor 15 or the like. The measuring unit 11 corresponds to the measuring unit.

The pulse sensor 13 is a sensor unit which detects pulse waves of the subject and measures the pulse rate, and is provided on the wrist-side surface of the measuring device 10 mounted on the wrist of the subject. The pulse sensor 13 is made up of a photoelectric sensor including a light emitting element and a light receiving element. Light is cast toward a living body from the light emitting element, and reflected light reflected by a blood vessel is received by the light receiving element. The pulse sensor 13 detects pulse waves of the subject, using a phenomenon that the light reflectance differs between the time of expansion of the blood vessel and the time of contraction. The pulse sensor 13 performs frequency resolution processing on data of the detected pulse waves, analyzes the signal intensity value of each frequency, and extracts a frequency spectrum corresponding to the pulse waves. Then, the pulse sensor 13 calculates the pulse rate per minute from the frequency of the frequency spectrum of the pulse waves and outputs the pulse rate as pulse data. The pulse sensor 13 is not limited to the photoelectric sensor. An ultrasonic sensor which detects the contraction of the blood vessel via ultrasonic waves and thus measures the pulse rate may be employed, and a sensor which causes a weak current to flow through the body from an electrode and thus measures the pulse rate, or the like, may be employed.

The body movement sensor 15 is a sensor unit including an acceleration sensor, as a preferable example, and measures changes in acceleration in one axial direction or at least two axial directions intersecting with each other. The body movement sensor 15 calculates various kinds of information related to the body movement of the subject, using data of the changes in acceleration, and outputs the information as activity data. Specifically, the body movement sensor 15 adds up the measured amount of change in acceleration and measures the magnitude of the body movement of the subject. Also, the body movement sensor 15 performs integration processing on the amount of change in acceleration and thereby performs frequency resolution processing on the amount of movement of the subject, thus measuring the pitch or the number of steps taken by the subject when walking, running or the like. Also, the body movement sensor 15 may include a gyro sensor, GPS (global positioning system) sensor or the like, and may be configured to be able to discriminate and measure more diverse body movements of the subject. The signal from the acceleration sensor can also be used in processing to restrain a body movement noise superimposed on a pulse wave signal when detecting the above pulse rate.

The measuring unit 11 is not limited to the configuration including the pulse sensor 13 and the body movement sensor 15, as a sensor unit, and may have a configuration including an environment sensor such as a temperature sensor or pressure sensor. With the environment sensor, external environment information (external temperature, position and the like) of the subject wearing the measuring device 10 can be taken in.

The display unit 17 is a display device which is configured with a display panel such as an LCD (liquid crystal display) and a light emitting element such as an LED (light emitting diode) and which carries out various displays based on display signals inputted from the control unit 27. On the display panel, various kinds of information calculated by the control unit 27 are displayed based on the data detected by the measuring unit 11 such as pulse rate, the number of steps taken, exercise intensity, and calories burned of the subject. The display panel may be configured to display a character string of advice for the subject received from the PC 30. For the light emitting element, a plurality of LEDs emitting light in a plurality of colors is used. Information to be reported to the subject is issued by a method corresponding to a light emitting pattern defined for each content. The information to be reported to the subject may include the content of advice for the subject received from the PC 30.

The operation unit 19 is an input device configured with a button switch or the like and outputs a signal of a button that is pressed, to the control unit 27. By this operation of the operation unit 19, various instructions such as an instruction to measure the pulse rate are inputted. The configuration of the operation unit 19 is not limited to this. Any configuration that enables a plurality of operations to be inputted may be employed, and a touch panel function may be provided for the display panel of the display unit 17.

The clocking unit 21 is configured with a crystal oscillator unit or the like made up of a crystal oscillator and an oscillator circuit, and has a clock function and a stopwatch function of the measuring device 10, and a clocking function such as generation of a sampling time used for the detection by the pulse sensor 13 and the body movement sensor 15. The clocked time of the clocking unit 21 is outputted to the control unit 27 as needed.

The communication unit 23 is a communication device for transmitting and receiving information used inside the device, to and from an information processing device outside the PC 30, under the control of the control unit 27. As a communication method of this communication unit 23, a wireless connection form utilizing the wireless communication 9, which is short-range wireless communication conforming to a predetermined communication standard, may be used, and activity data can be transmitted to the PC 30 even while the subject is doing an activity such as exercise. The communication unit 23 is not limited to short-range wireless communication and may be configured to be able to transmit and receive various data and information via wired communication.

The storage unit 25 is made up of a storage device such as a ROM (read only memory), flash ROM, or RAM (random aces memory), and stores the control program of the measuring device 10, various programs, data and the like to realize various functions such as the function of measuring pulse rates, exercise intensity, and calories burned. Also, the storage unit 25 has a work area for temporarily storing currently processed data in various kinds of processing and results of processing or the like.

The control unit 27 is a control device and computing device which comprehensively controls each part of the measuring device 10 according to various programs such as the control program stored in the storage unit 25, and is configured with a processor such as a CPU (central processing unit) or DSP (digital signal processor).

(Configuration of PC 30)

The PC 30 is made up of a display unit 31, an operation unit 33, a clocking unit 35, a communication unit 37, a storage unit 40, and a control unit 60 or the like.

For the display unit 31, a liquid crystal panel is employed as a preferable example. Advice or the like for the subject generated by the control unit 60 is displayed. A touch panel may be provided on the display surface. The operation unit 33 is an input device such as a keyboard or mouse. The clocking unit 35 is a real-time clock and has clocking functions such as calendar function, clock function, and stopwatch function, for example. The communication unit 37 is a network adapter and transmits and receives activity data and advice data to and from the measuring device 10 via the wireless communication 9 or wired communication.

The storage unit 40 is a hard disk drive (HDD) and a solid state drive (SSD) or the like and is managed by a file system. In the storage unit 40, a control program (not illustrated) executed by the control unit 60 and variables, data and the like used in the control program are stored. Also, in the storage unit 40, a motivation determination table 41, an advice correspondence table 43, advice wording data 45, and personal data 50 or the like are stored.

The motivation determination table 41 is a table in which the corresponding relations between trends of change in the achievement state information and the amount of action information of the subject, and the corresponding states of motivation are defined. Specifically, the motivation determination table 41 is a table loaded in such a way that the corresponding relations shown in the view explaining the result of determination on achievability (FIG. 1) and the view explaining the result of determination on urgency (FIG. 2) can be referred to by a motivation determination unit 77

(described later). The level of achievability and urgency is defined by "high", "middle", or "low", for each combination of trends of changes in the achievement state and the amount of action.

The advice correspondence table 43 is a table in which advice corresponding to each level of achievement and urgency is defined. Reference targets in the advice wording data 45 that match the respective levels of achievability "high", "middle", and "low" and the levels of urgency "high", "middle", and "low" defined in the motivation determination table 41 are stored.

Figure 9:
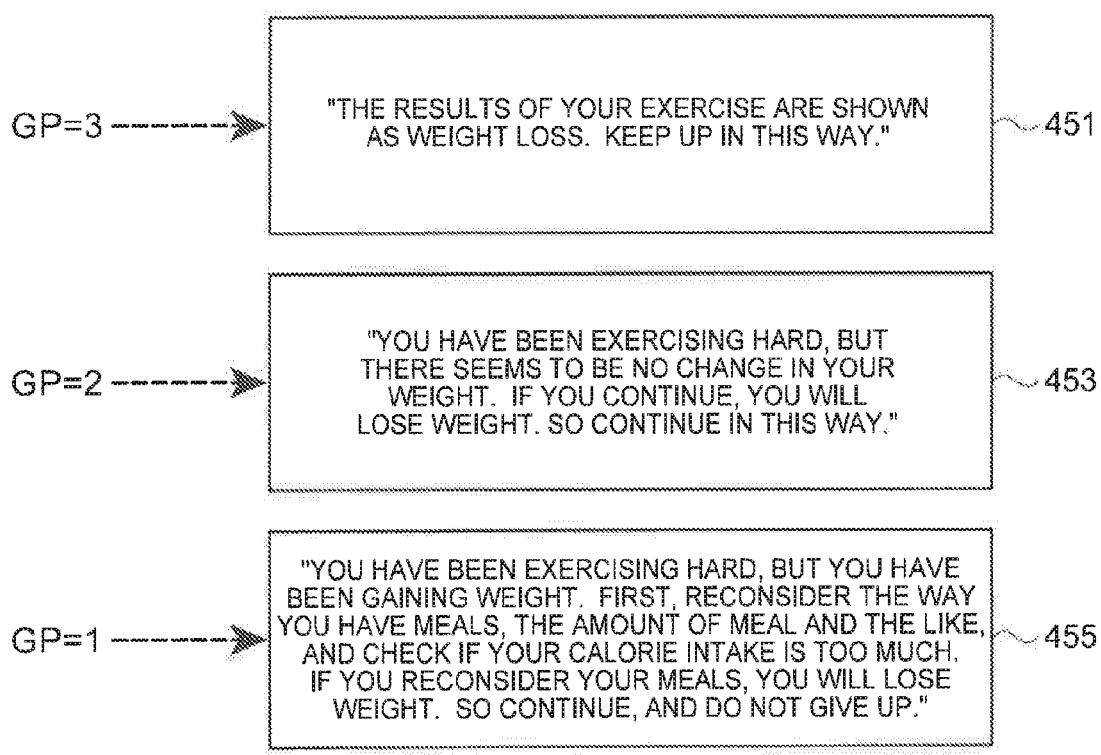
FIG. 9 is a display example of advice corresponding to the state of achievability.
Figure 10:
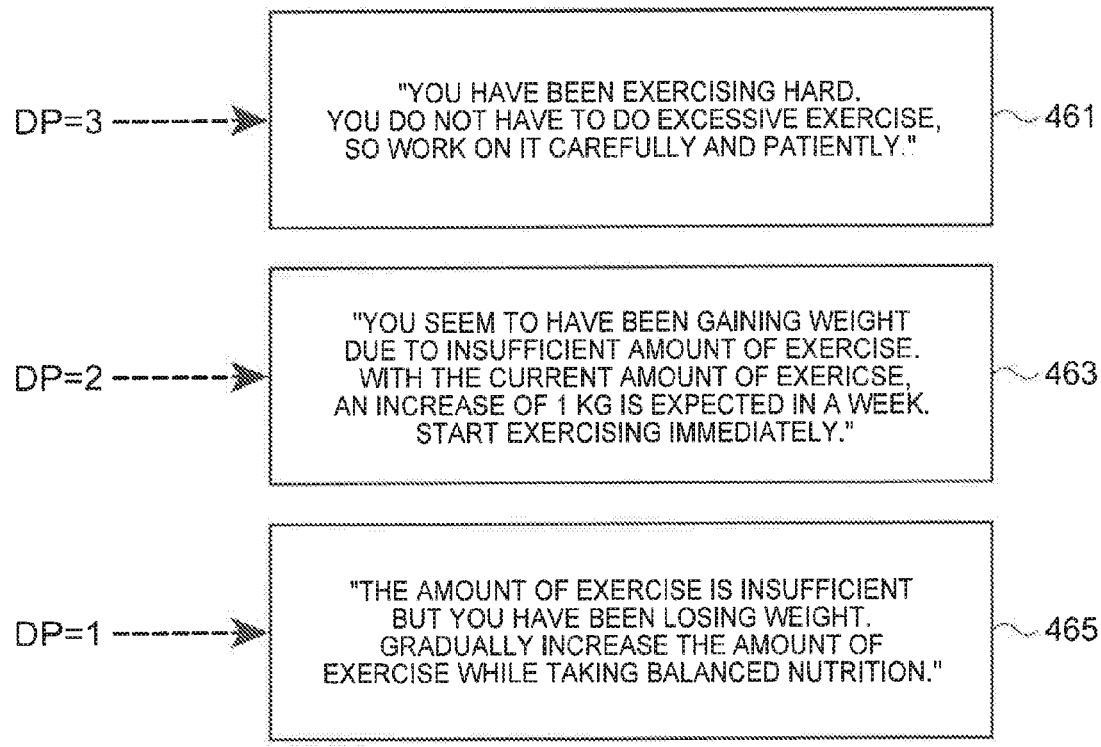
FIG. 10 is a display example of advice corresponding to the state of urgency.

The advice wording data 45 is character string data in which advice character strings are stored. In the character string data, character strings of various expressions are prepared and referred to from the advice correspondence table 43. The advice display examples shown in FIG. 9 and FIG. 10 are examples in which advice wording is read out from the advice wording data 45 and displayed on the display unit 31.

The personal data 50 is data including personal information about the subject and is made up of goal information data 51, achievement state data 53, activity data 55 and the like.

The goal information data 51 is data generated from information acquired from the subject at the time of setting the goal. At least data indicating the state of the subject at the time of setting the goal, the state at the time of achieving the goal, the period until the achievement of the goal, the content of the action to achieve the goal, the amount of action until the achievement of the goal, and the regular check period are stored. The check period corresponds to the predetermined period.

The achievement state data 53 is data indicating the achievement data of the goal of the subject. At least the result of the achievement state is stored for each check period. For example, if the goal of the subject is a goal related to weight loss, the body weight and the weight lost are stored for each check period.

The activity data 55 is activity data of the subject received from the measuring device 10. The activity data measured from the start of the action is stored in time series. The activity data 55 includes information such as pulse data, acceleration data, data of the number of steps taken, and pitch data.

The control unit 60 is a CPU and controls each part such as the display unit 31, the operation unit 33, the clocking unit 35, the communication unit 37, and the storage unit 40, forming the PC 30. The control unit 60 has an advice processing unit 70 as a functional unit. However, these functions units are simply an example and not all the functional units need to be essential components. Also, functional units other than these may be essential components.

The advice processing unit 70 is a functional unit which generates advice for the subject and is configured with functional units such as an achievement state acquisition unit 71, an activity data acquisition unit 73, an amount of action calculation unit 75, a motivation determination unit 77, and an advice generation unit 79.

The achievement state acquisition unit 71 acquires information of the achievement state of the subject acting to achieve the goal. Specifically, by controlling the display unit 31 and the operation unit 33, information of the achievement state inputted by the subject is acquired at least for each check period. For example, if the goal to achieve is weight loss of 10 kg and the check period is every month, the subject is prompted to input the weight lost that is measured at least every month.

Also, depending on the goal that is set, information of the achievement state can be acquired by receiving measurement data measured by the measuring device 10 or another external measuring device, via the communication unit 37. For example, if the goal is to finish a full marathon within four hours, data of the distance traveled may be acquired from the measuring device 10 and the time taken for running the distance of a full marathon may be used as the information of the achievement state. Also, as another example, measurement data measured by an external measuring device such as a body weight scale, body fat meter, or body composition monitor, having a communication function, may be received via the communication unit 37 and information of the achievement state may be acquired.

The information of the achievement state corresponds to the achievement state information. The check period corresponds to the predetermined period. The achievement state acquisition unit 71 corresponds to the achievement state acquisition unit.

The activity data acquisition unit 73 acquires activity data from the measuring device 10. Specifically, by controlling the communication unit 37, the communication with the measuring device 10 is established, and activity data measured by the measuring device 10 is received and stored in the storage unit 40 as the activity data 55.

The amount of action calculation unit 75 calculates the amount of action information of the subject, using the activity data 55. Specifically, activity data is read from the activity data 55, and the amount of action is calculated, thus calculating, for each check period, the amount of action information accumulated during the check period. Since the amount of action is the amount of the action taken to reach the achievement state of the goal to be achieved by the subject, if the goal is different, the type of the amount of action calculated may be different.

For example, if the goal to achieve is a goal related to weight loss, calories burned are calculated from activity data taken during cardio exercise. The cumulative amount of calories burned during the check period is calculated as the amount of action information. As a method for calculating calories burned, a known method such as a calculation method based on the correlation between pulse rate data and calories burned during cardio exercise, or a calculation method in which exercise intensity is calculated from pulse rate data or acceleration data and then the calories burned for each exercise intensity is multiplied by the time elapsed is employed.

For example, if the goal to achieve is to reduce the target time of a full marathon, the distance traveled is calculated. The distance traveled may be calculated using GPS location information and acceleration data included in the activity data 55.

The amount of action calculation unit 75 corresponds to the amount of action calculation unit.

The motivation determination unit 77 determines the state of achievability and the state of urgency, which form motivation. Specifically, the trends of change at the start and end of the check period are calculated with respect to the achievement state and the amount of action calculated by the achievement state acquisition unit 71 and the amount of action calculation unit 75. From the relation between the trend of change in the achievement state and the trend of change in the amount of action, the state of achievability is derived in the three levels of "high", "middle", and "low", as shown in FIG. 1, and the state of urgency shown in FIG. 2 is derived in the three levels of "high", "middle", and "low".

The motivation determination unit 77 corresponds to the motivation determination unit.

The advice generation unit 79 generates advice suitable for the states of achievability and urgency of motivation. Specifically, referring to the advice correspondence table 43, advice wording corresponding to the state of motivation determined by the motivation determination unit 77 is acquired.

The advice generation unit 79 corresponds to the advice generation unit.

(Flow of Advice Generation Method)

Figure 5:
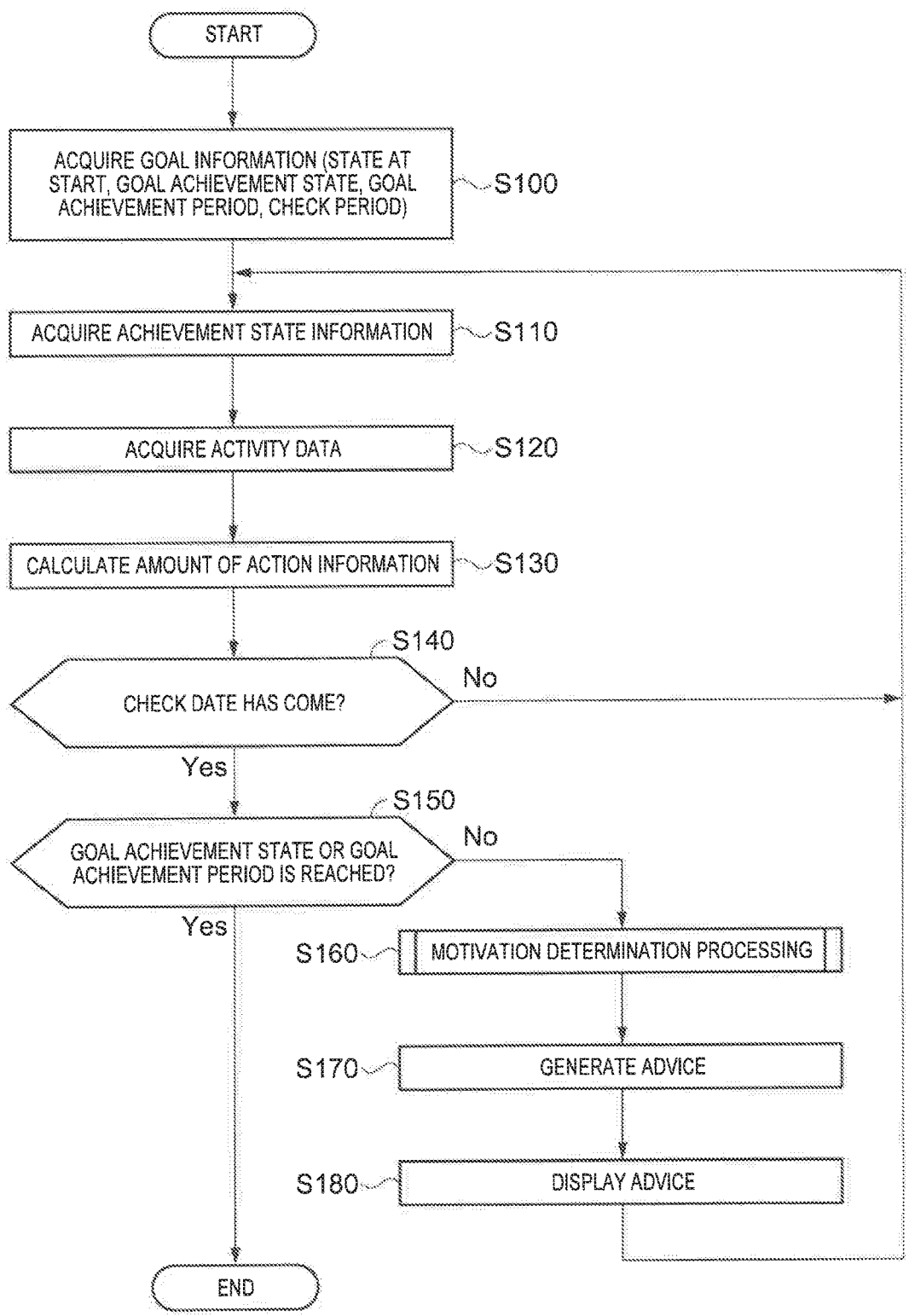
FIG. 5 is a flowchart showing a flow of advice generation processing.

FIG. 5 is a flowchart showing the flow of advice generation processing. This flow is a flow of processing executed by the control unit 60 controlling each unit including the display unit 31, the operation unit 33, the clocking unit 35, the communication unit 37, and the storage unit 40 or the like.

This flow corresponds to the advice generation processing. Also, before this flow is executed, the activity status of the subject is acquired by the measuring unit 11 of the measuring device 10 and the activity data is transmitted to the PC 30 from the measuring device 10. The flow of these processes corresponds to the measuring process and included in the advice generation method.

In Step S100, the goal information is acquired. The information of the state at the start, the goal achievement state, the goal achievement period, and the check period is acquired from the goal information data 51 stored in the storage unit 40. If the goal information data 51 is not generated yet, the operation unit 33 and the display unit 31 are controlled to display a screen prompting an input, and the goal information is thus acquired from the subject.

In Step S110, the achievement state information is acquired. The achievement state data of the subject is acquired from the achievement state data 53 stored in the storage unit 40. If the achievement state data stored in the achievement state data 53 is not updated, the operation unit 33 and the display unit 31 are controlled to display a screen prompting an input, and the achievement state data is thus acquired from the subject. Meanwhile, if the achievement state information is to be received from the measuring device 10 or an external device, the communication with each device is established and the achievement state data is acquired. The newly acquired achievement state data is stored in the achievement state data 53. In this step, the function of the achievement state acquisition unit 71 is implemented.

This step corresponds to the achievement state acquisition process.

In Step S120, the activity data is acquired. The activity data of the subject is acquired from the activity data 55 stored in the storage unit 40. If the activity data stored in the activity data 55 is not updated, the communication unit 37 is controlled to establish the communication with the measuring device 10, and the activity data accumulated in the measuring device 10 is received. The newly received activity data is stored in the activity data 55. In this step, the function of the activity data acquisition unit 73 is implemented.

In Step S130, the amount of action information is calculated. Specifically, the amount of action is calculated from the activity data acquired in Step S120. The calculated amount of action is added up and the cumulative value of the amount of action from the start of the action is thus calculated. In this step, the function of the amount of action calculation unit 75 is implemented.

This step corresponds to the amount of action calculation process.

In Step S140, whether the check date has come or not is determined. Whether or not the check period has passed since the start of the action or since the previous check date is determined. If the check date has come (Step S140; Yes), the processing goes to Step S150. If the check date has not come (Step S140; No), the processing returns to Step S110 and Steps S110 to S130 are repeated.

In Step S150, whether the goal achievement state or the goal achievement period is reached or not is determined. If the achievement state acquired in Step S110 has reached the goal achievement state acquired in Step S100, or if the check date has reached the goal achievement period acquired in Step S100 (Step S150; Yes), this flow ends. If the goal achievement state is not reached and the goal achievement period is not reached (Step S150; No), the processing goes to Step S160.

In Step S160, the motivation determination processing is executed. In this step, the function of the motivation determination unit 77 is implemented and the state of motivation of the subject is determined. As the state of motivation, the states of achievability and urgency, which form motivation, are determined. The flow of the motivation determination processing will be described in detail, using FIG. 6 to FIG. 8.

This step corresponds to the motivation determination process.

In Step S170, advice is generated. Specifically, advice wording corresponding to the state of motivation determined in Step S160 is generated with reference to the advice correspondence table 43 and the advice wording data 45. In this step, the function of the advice generation unit 79 is implemented.

This step corresponds to the advice generation process.

In Step S180, the advice is displayed. The advice wording generated in Step S170 is outputted to the display unit 31. An example of advice displayed for each state of motivation that is determined will be described later using FIG. 9 and FIG. 10.

(Flow of Motivation Determination Processing)

Figure 6:
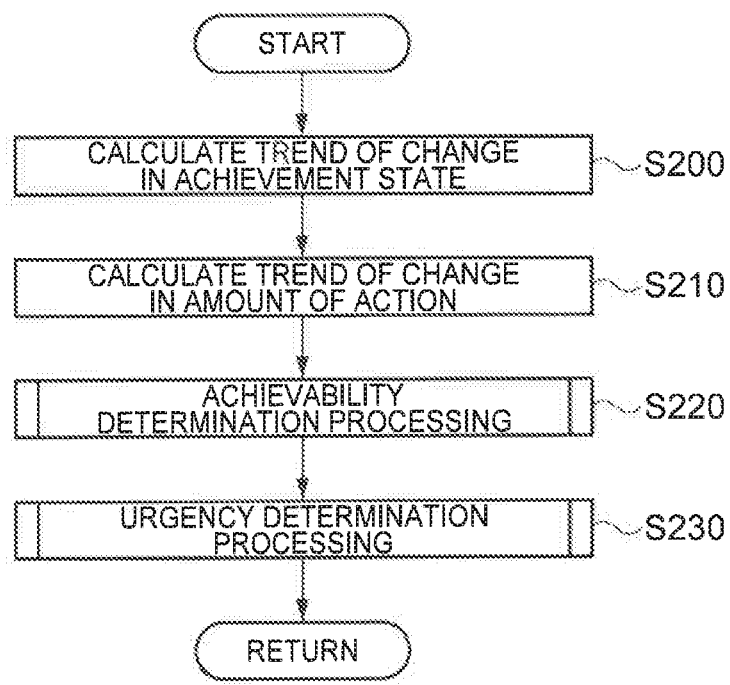
FIG. 6 is a flowchart showing a flow of motivation determination processing.
Figure 7:
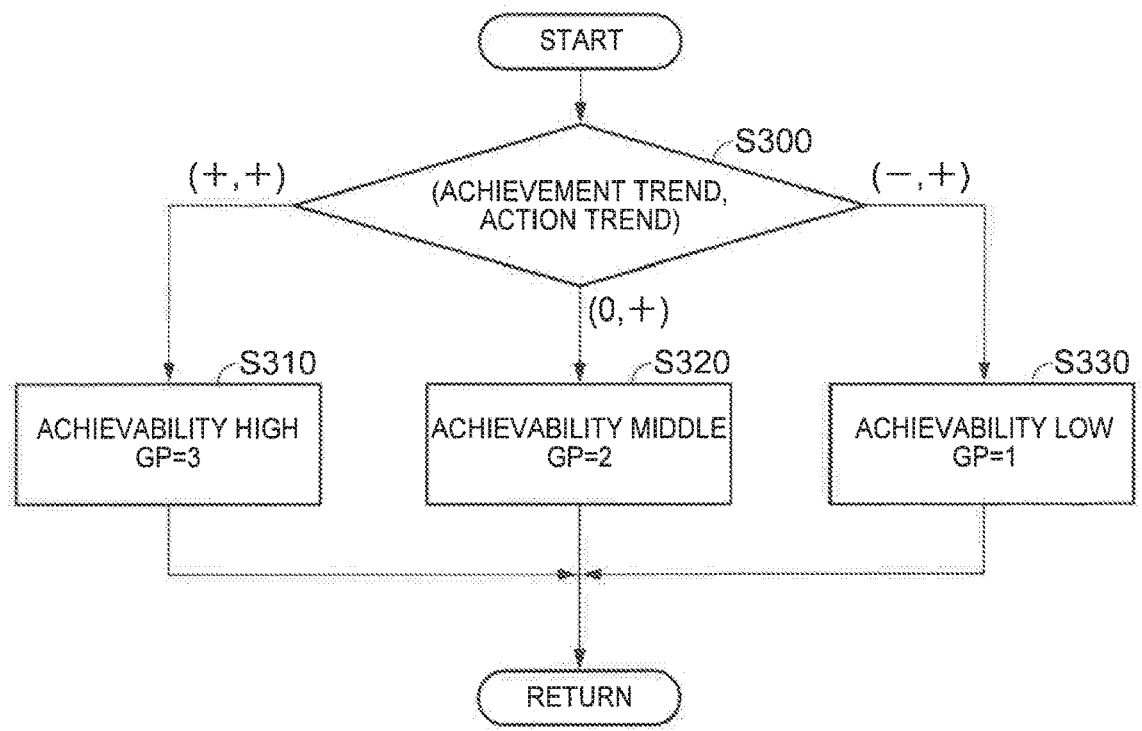
FIG. 7 is a flowchart showing a flow of achievability determination processing.
Figure 8:
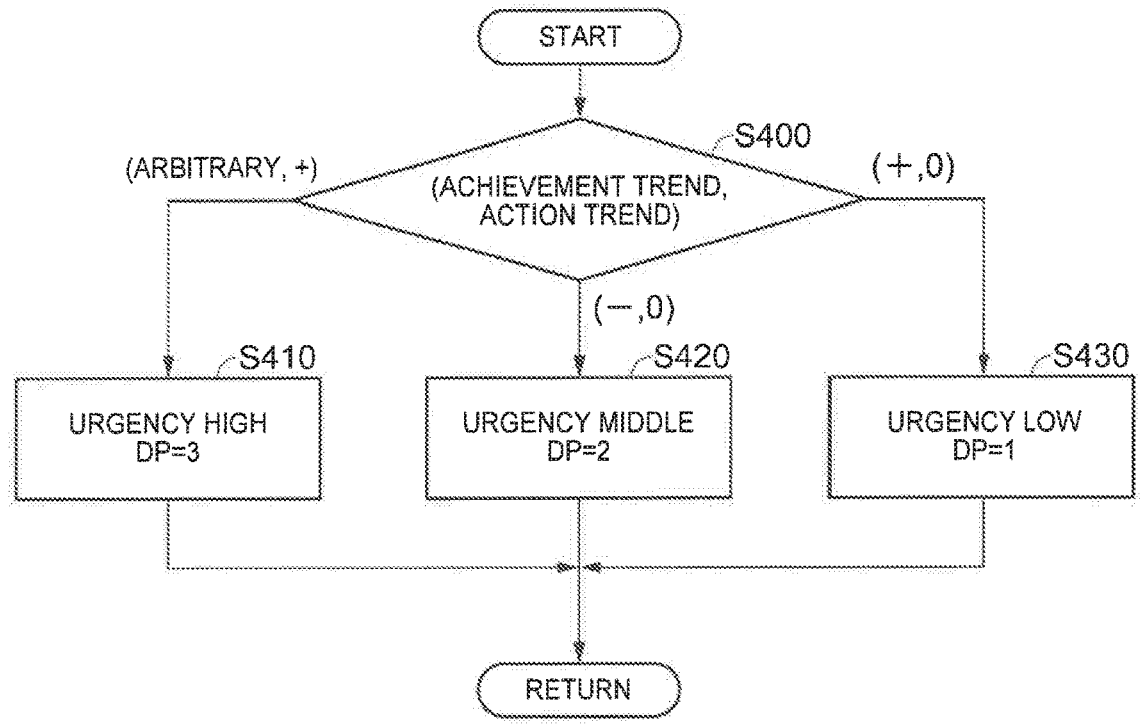
FIG. 8 is a flowchart showing a flow of urgency determination processing.

FIG. 6 is a flowchart showing the flow of the motivation determination processing. FIG. 7 is a flowchart showing the flow of achievability determination processing. FIG. 8 is a flowchart showing the flow of urgency determination processing.

Step S200 to Step S230 shown in FIG. 6 are steps explaining details of the flow of the processing of Step S160 shown in FIG. 5.

In Step S200, the trend of change in the achievement state is calculated. Specifically, the difference in the achievement state between the start and the end of the check period is calculated, and which of the + trend, the − trend, and the 0 trend the trend of change is, is decided.

In Step S210, the trend of change in the amount of action is calculated. Specifically, the difference in the cumulative value of the amount of action between the start and the end of the check period is calculated, and which of the + trend and the 0 trend the trend of change is, is decided.

In Step S220, the achievability determination processing is carried out. Which level of "high", "middle", and "low" the state of achievability of the subject is, is determined. Details of this step will be described using Step S300 to Step S330 (FIG. 7).

In Step S230, the urgency determination processing is carried out. Which level of "high", "middle", and "low" the state of urgency of the subject is, is determined. Details of this step will be described using Step S400 to Step S430 (FIG. 8).

Now shift to FIG. 7.

In Step S300, the state of achievability is determined based on the results of the trend of change in the achievement state (achievement trend) and the trend of change in the amount of action (action trend). If the result of combination of (achievement trend, action trend) is (+ trend, + trend), the processing goes to Step S310. If the combination is (0 trend, + trend), the processing goes to Step S320. If the combination is (− trend, + trend), the processing goes to Step S330.

In Step S310, the achievability is determined as "high" and 3 is substituted for a variable GP.

In Step S320, the achievability is determined as "middle" and 2 is substituted for the variable GP.

In Step S330, the achievability is determined as "low" and 1 is substituted for the variable GP.

Now shift to FIG. 8.

In Step S400, the state of urgency is determined based on the results of achievement trend and action trend. If the result of combination of (achievement trend, action trend) is (arbitrary, + trend), the processing goes to Step S410. If the combination is (− trend, 0 trend), the processing goes to Step S420. If the combination is (+ trend, 0 trend), the processing goes to Step S430.

In Step S410, the urgency is determined as "high" and 3 is substituted for a variable DP.

In Step S420, the urgency is determined as "middle" and 2 is substituted for the variable DP.

In Step S430, the urgency is determined as "low" and 1 is substituted for the variable DP.

(Display Example of Advice)

FIG. 9 is a display example of advice corresponding to the state of achievability.

If the achievability is determined as "high" in the achievability determination processing, 3 is substituted for the variable GP. In the case of GP=3, advice 451 is displayed. In the advice 451, since the subject feels that the achievability is high, advice with a content to maintain the high state is generated and displayed.

If the achievability is determined as "middle", 2 is substituted for the variable GP. In the case of GP=2, advice 453 is displayed. In the advice 453, since the subject does not feel that the achievability is as high as the above "high" level, advice with a content suggesting that the achievement trend will change to the + trend if the subject changes the action trend to the + trend and continues that trend, is generated and displayed.

If the achievability is determined as "low", 1 is substituted for the variable GP. In the case of GP=1, advice 455 is displayed. In the advice 455, since the subject feels that the achievability is low, advice with a content which makes the subject notice the cause of the achievement trend being the − trend and thus theoretically leads the subject to take some measures so as to eliminate the psychological state that the achievability is low, is generated and displayed.

FIG. 10 is a display example of advice corresponding to the state of urgency.

If the urgency is determined as "high" in the urgency determination processing, 3 is substituted for the variable DP. In the case of DP=3, advice 461 is displayed. In the advice 461, since the subject feels that the urgency is high, advice with a content which leads the subject toward not taking excessive action because of the high urgency is generated and displayed.

If the urgency is determined as "middle", 2 is substituted for the variable DP. In the case of DP=2, advice 463 is displayed. In the advice 463, since the subject does not feel that the urgency is as high as the above "high" level, if the action trend is left as the 0 trend, the achievement trend is left as the − trend. Therefore, advice with a content which specifically expresses a conclusion that will be reached if this state continues is generated and displayed.

If the urgency is determined as "low", 1 is substituted for the variable DP. In the case of DP=1, advice 465 is displayed. In the advice 465, since the urgency of the subject is low, advice with a content including an expression to change the action trend toward the + trend is generated and displayed.

As described above, the advice generation system 1 according to the embodiment can achieve the following effects.

According to the advice generation system 1, the motivation determination unit 77 quantifies the levels of the elements of achievement and urgency forming the state of motivation, based on the achievement state information of the subject and the amount of action information of the subject. Specifically, the state of achievability is expressed by each level of "high", "middle", or "low", and the state of urgency is expressed by each level of "high", "middle", or "low". Also, the information used for the determination on motivation is the activity data of the subject measured by the measuring unit 11 and the achievement state information acquired from the subject, which are the information actually measured from the subject.

In this way, the motivation determination unit 77 realizes the quantification of motivation, which is the psychological state of the subject, based on the information directly measured from the subject.

The advice generation unit 79 can select, from the advice wording data 45, the most suitable advice wording to maintain the states of achievability and urgency at a high level for each level expressing the quantified states of achievability and urgency, and thus can generate advice.

Therefore, the advice generation system 1 can generate advice reflecting the state of motivation of the subject and can provide the subject with advice corresponding to the status of motivation of the subject.

Embodiment 2

Next, Embodiment 2 will be described using FIG. 11, FIG. 12, FIG. 13, and FIG. 14.

While the advice generation system 1 according to Embodiment 1 is a system which generates advice for one subject, an advice generation system 2 according to Embodiment 2 is different in that the advice generation system 2 generates advice for a plurality of subjects and that the generated advice is generated with reference to information of other subjects than the subject him/herself. The other features are similar to those of Embodiment 1. Also, components similar to those of Embodiment 1 are similarly applied to this embodiment. In FIG. 11 to FIG. 14, components similar to those of Embodiment 1 are denoted by reference signs similar to those in the illustrations explained in Embodiment 1, and detailed explanation thereof is omitted.

Figure 11:
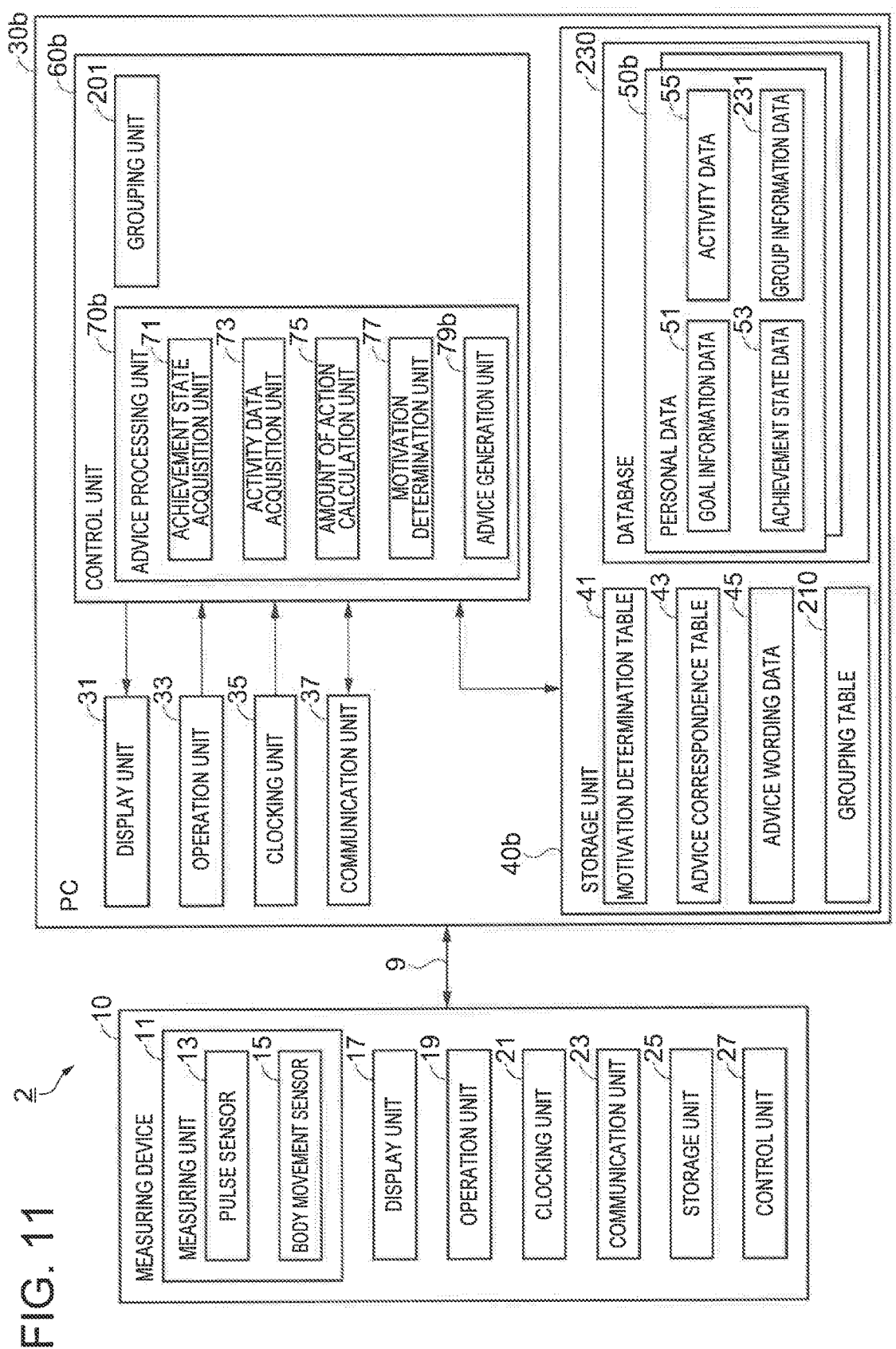
FIG. 11 is a block diagram showing a schematic configuration of an advice generation system according to Embodiment 2.

FIG. 11 is a block diagram showing a schematic configuration of the advice generation system according to Embodiment 2. The advice generation system 2 is made up of a measuring device 10, a PC 30b and the like, and various data are transmitted and received between the two via wireless communication 9. The measuring device 10 and the wireless communication 9 are the same components as those of Embodiment 1. Hereinafter, different components from those of Embodiment 1 will be described, mainly with respect to the PC 30b.

The PC 30b is configured with a storage unit 40b, a control unit 60b and the like.

The storage unit 40b has a grouping table 210, a database 230 and the like.

The grouping table 210 is a table in which an objective and the degree of difficulty to achieve the objective are defined. The objective and the degree of difficulty are derived from information at the time of setting the goal of the subject, by a grouping unit 201, described later.

The storage unit 40b corresponds to the storage unit.

FIG. 12 is a view explaining an example of the grouping table. FIG. 12(a) is an example of a group definition table. FIG. 12(b) is an example of a difficult degree definition table using weight loss target as an example. FIG. 12(c) is an example of a difficulty degree definition table using full marathon target time as an example. FIG. 12(d) is an example of a difficulty degree definition table using half marathon target time as an example.

In a group definition table 211 shown in FIG. 12(a), "objective" is described in the direction of column, and "degree of difficulty" is described in the direction of row.

The "objective" is a matter that should be realized for health improvement and enhancement of athletic ability. In the group definition table 211, as examples of the "objective", "weight loss" is given as an objective A, "full marathon" is given as an objective B, and "half marathon" is given as an objective C. The "weight loss" indicates the objective of loading body weight. The "full marathon" indicates the objective of reducing the completing time of a full marathon. The "half marathon" indicates the objective of reducing the completing time of a half marathon.

The "degree of difficulty" is the degree of difficulty in achieving the "objective". In order from the lowest degree of difficulty (easiest), "level 1", "level 2", "level 3", "level 4", and "level 5" are defined. The "level 5" indicates the highest degree of difficulty of these (most difficult).

In the group definition table 211, in the sections where the "objective" and the "degree of difficulty" cross each other, group names for groupings are defined. For example, for the objective A of "weight loss", group names corresponding to the respective levels of the degree of difficulty are defined, and groups A1 to A5 are defined for the levels 1 to 5, respectively. Similarly, for the objective B of "full marathon", groups B1 to B5 are defined corresponding to the levels 1 to 5 of the degree of difficulty. For the objective C of "half marathon," groups C1 to C5 are defined corresponding to the levels 1 to 5 of the degree of difficulty.

A difficulty degree definition table 213 shown in FIG. 12(b) is a table which decides the "degree of difficulty" for the objective A of "weight loss". "Weight loss target" is described in the direction of column in the difficulty degree definition table 213, and "current state" is described in the direction of row. The "weight loss target" indicates the state at the time of achieving the goal and here indicates the target weight to lose. The descriptions of "30 kg", "20 kg", and "10 kg" indicate the target weights 30 kg, 20 kg, and 10 kg to lose respectively from the current body weight. The "current state" indicates the current body weight. For example, the body weight measured at the time of setting the goal is applied. The row where the "current state" is "100 kg" indicates that the current body weight is 100 kg or above. The current state of "90 kg" indicates that the current body weight is 90 kg or above, and below 100 kg. The current state of "80 kg" indicates that the current body weight is 80 kg or above, and below 90 kg.

In the sections where the "weight loss target" and the "current state" cross each other, levels 1 to 5 indicating levels of the degree of difficulty are defined. For example, if the current state is "100 kg" and the weight loss target is "30 kg", the "level 3" is defined. If the current state is "100 kg" and the weight loss target is "20 kg", the "level 2" is defined. This shows that, if the current body weight is the same, the weight loss target of "20 kg" is easier to achieve than "30 kg". As the level of the degree of difficulty, the level 2 lower than the level 3 of "30 kg" is the level of "20 kg".

A difficulty degree definition table 215 shown in FIG. 12(c) is a table which decides the "degree of difficulty" for the objective B of "full marathon". "Target" is described in the direction of column in the difficulty degree definition table 215, and "current state" is described in the direction of row. The "target" indicates the state at the time of achieving the goal and here indicates the target completing time. The descriptions of "2 h 30 m", "3 h", "3 h 30 m", "4 h", and "4 h 30 m" indicate that the target completing time is 2 hours 30 minutes or shorter, longer than 2 hours 30 minutes and equal to or shorter than 3 hours, longer than 3 hours and equal to or shorter than 3 hours 30 minutes, longer than 3 hours 30 minutes and equal to or shorter than 4 hours, and longer than 4 hours and equal to or shorter than 4 hours 30 minutes, respectively, in order. The "current state" indicates the completing time based on the current ability. The description of "3 h" indicates that the current completing time of a full marathon is 3 hours or shorter. Similarly, "3 h 30 m", "4 h", "4 h 30 m", and "5 h" indicate that the current completing time is longer than 3 hours and equal to or shorter than 3 hours 30 minutes, longer than 3 hours 30 minutes and equal to or shorter than 4 hours, longer than 4 hours and equal to or shorter than 4 hours 30 minutes, and longer than 4 hours 30 minutes and equal to or shorter than 5 hours, respectively, in order.

In the sections where the "target" and the "current state" cross each other, levels 1 to 5 indicating levels of the degree of difficulty are defined. For example, the degree of difficulty for a subject whose current completing time is 3 hours aims to achieve 2 hours 30 minutes is the level 5, which is a high level. The degree of difficulty for a subject whose current completing time is 5 hours aims to achieve 4 hours 30 minutes is the level 1, which is a low level. In the sections where a slant line is given, no element is defined. For example, in the case where a subject whose current completing time is 5 hours aims to achieve the completing time of 3 hours 30 minutes, if the subject continues training and shortens the completing time, the entry of "current state" is moved up and the degree of difficulty increases by each stage, such as, from the level 1 to the level 2 and then to the level 3.

A difficulty degree definition table 217 shown in FIG. 12(d) is a table which decides the "degree of difficulty" for the objective C of "half marathon". "Target" is described in the direction of column in the difficulty degree definition table 217, and "current state" is described in the direction of row. The difficulty degree definition table 217 is different from the difficulty degree definition table 215 in the times set as the "target" and "current" completing times, but similar in the other definition contents.

Back to FIG. 11, the database 230 forming the storage unit 40b will be described. The database 230 is a database engine such as a relational database and manages a plurality of personal data 50b.

In the personal data 50b, information of one subject is stored. As the database 230, the personal data 50b of a plurality of subjects are stored. In the database 230, a database program or the like for searching for various data such as goal information data 51, achievement state data 53, activity data 55, and group information data 231 contained in the personal data 50b, by various conditional equations, is stored as well. The database program is read and executed by the control unit 60b.

In the group information data 231, information of the group to which the subject belongs is stored. A group name is stored as the information of the group. The group name is information such as the groups A1 to A5 shown in FIG. 12 (a).

The personal data 50b managed in the database 230 is not limited to personal data of a subject who is executing a goal achievement action, and personal data of a subject who has finished a goal achievement action may be stored as well. Also, personal data of a subject who is successful in achieving the goal and a subject who has finished while still unable to achieve the goal, or the like, may be stored. By storing information of subjects in such diverse states, it is possible to generate advice including abundant information.

The control unit 60b is configured with functional units such as an advice processing unit 70b and a grouping unit 201. Also, the advice processing unit 70b has an advice generation unit 79b.

The grouping unit 201 decides the group to which the subject belongs. Specifically, the state at the time of setting the goal (before starting the action) and the state at the time of achieving the goal are acquired from the goal information acquired from the subject. From the state at the time of achieving the goal, the "objective" of the subject is determined and the objective corresponding to the entry of the "objective" in the group definition table 211 is selected. Next, which level the "degree of difficulty" is, is decided, using the information of the state at the time of setting the goal and the state at the time of achieving the goal and referring to the difficulty degree definition table 213 (215, 217). As the "objective" and the "degree of difficulty" are decided, the group name for the crossing elements is decided. The decided group name is stored as the group information data 231. The subject is regarded as belonging to the group of the decided group name.

The grouping unit 201 corresponds to the grouping unit.

The advice generation unit 79b generates advice for the subject, referring to the information of the personal data within the group to which the subject belongs. Specifically, the subjects in the same group defined in the group definition table 211 are a group of subjects who have a common objective and a common degree of difficulty to achieve the goal. Therefore, the subject has an affinity to the information of the subjects in the same group, as information of the subjects having the same experience, according to the law of similarity (psychology). The information of a subject who has successfully achieved the goal is effective in increasing the element of achievability of motivation. On the contrary, the information of a subject who has failed to achieve the goal is effective in increasing the element of urgency of motivation.

Referring to the achievement state data 53 and the activity data 55 from the personal data 50b of the same group as the subject, the advice generation unit 79b acquires achievement state information including success and failure from the achievement state data 53 and acquires information of the action content from the activity data 55. Based on the achievement state information and the information of the action content that are acquired, advice for the subject currently taking action is generated.

Figure 13:
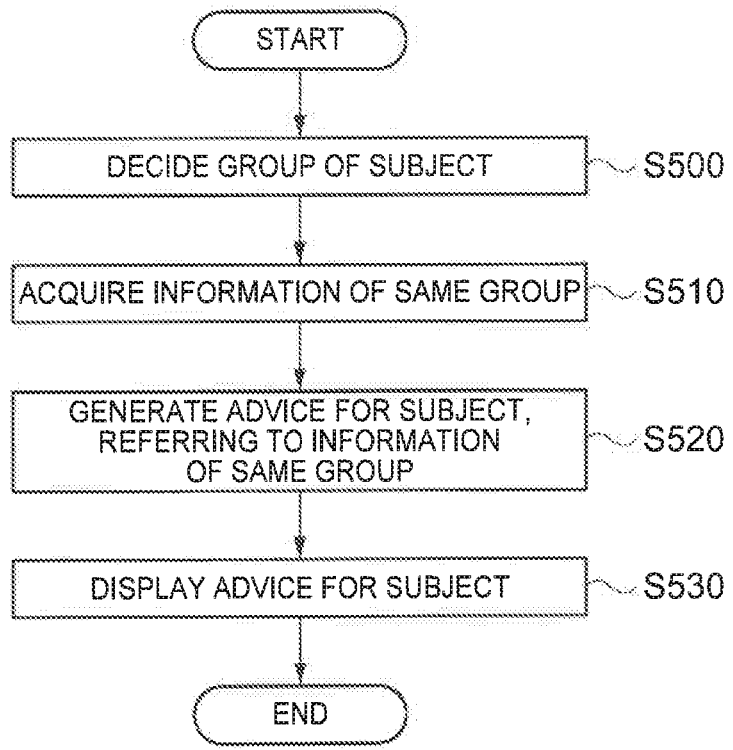
FIG. 13 is a flowchart showing a flow of advice generation processing with reference to groups.

FIG. 13 is a flowchart showing the flow of advice generation processing referring to groups. This flow is a flow of processing executed by the control unit 60b controlling each unit including the display unit 31 and the storage unit 40b.

In Step S500, the group of the subject is decided. The group to which the subject belongs is decided referring to the grouping table 210 based on the goal information acquired from the subject.

In Step S510, the information of the same group is acquired. Specifically, the information of other subjects in the group to which the subject belongs is acquired. Specifically, the personal data 50b with the same group name is acquired from the database 230. From the acquired personal data 50b, the information of the activity data 55 with which the achievement state data 53 shows that the goal is achieved, is acquired as information for the achievement of the goal (success information). Meanwhile, from the acquired personal data 50b, the information of the activity data 55 with which the achievement state data 53 shows that the goal is not achieved, is acquired as information for the non-achievement of the goal (failure information).

In Step S520, advice for the subject is generated referring to the information of the same group. Specifically, advice wording for the subject is generated based on the information acquired in Step S510. In the case of the success information, the information of the activity data 55 is searched for information about regular actions, and the resulting information is converted into wording. For example, if a value of low exercise intensity of jogging or the like is maintained for approximately an hour, every day, early in the morning, wording such as "People carrying out an exercise with the exercise intensity of light jogging or the like for 60 minutes or longer early in the morning tend to achieve the goal" are generated.

In Step S530, the advice for the subject is displayed. The advice generated in Step S520 is outputted to the display unit 31.

Figure 14:
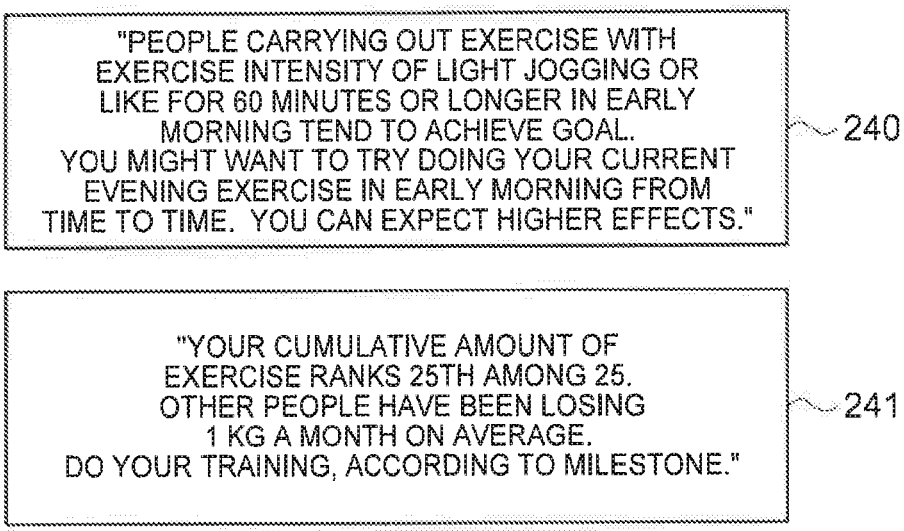
FIG. 14 is a display example of advice with reference to groups.

FIG. 14 is a display example of advice referring to groups. As advice 240, wording of "People carrying out exercise with exercise intensity of light jogging or the like for 60 minutes or longer in early morning tend to achieve the goal," is generated from the success information of the same group. The activity data 55 of the subject and the success information of the same group are compared, and wording of "You might want to try doing your current evening exercise in early morning from time to time. You can expect higher effects," is generated.

As advice 241, wording of "Your cumulative amount of exercise ranks $25^{th}$ among 25," is generated from the activity data 55 of the subject and statistical information of the other subjects in the same group. Wording of "Other people have been losing 1 kg a month on average. Do your training, according to a milestone," is generated from the success information of the same group.

As described above, the advice generation system 2 according to the embodiment can achieve the following effects in addition to the effects of the foregoing embodiment.

According to the advice generation system 2, the group to which the subject belongs is decided by the grouping unit 201. It means that all of the subjects belonging to the group have a common objective and a common degree of difficulty. The advice generation unit 79b generates advice wording which increases the element of achievability of the motivation of the subject or advice wording which increases the element of urgency of the motivation from information of the personal data 50b of the subject and the other personal data 50b in the same group.

Thus, as the advice generation system 2 provides the subject with advice generated based on experience information of other subjects having a common objective and a common degree of difficulty, the subject can take an action to achieve the goal in the state where higher motivation is maintained.

Embodiment 3

Figure 15:
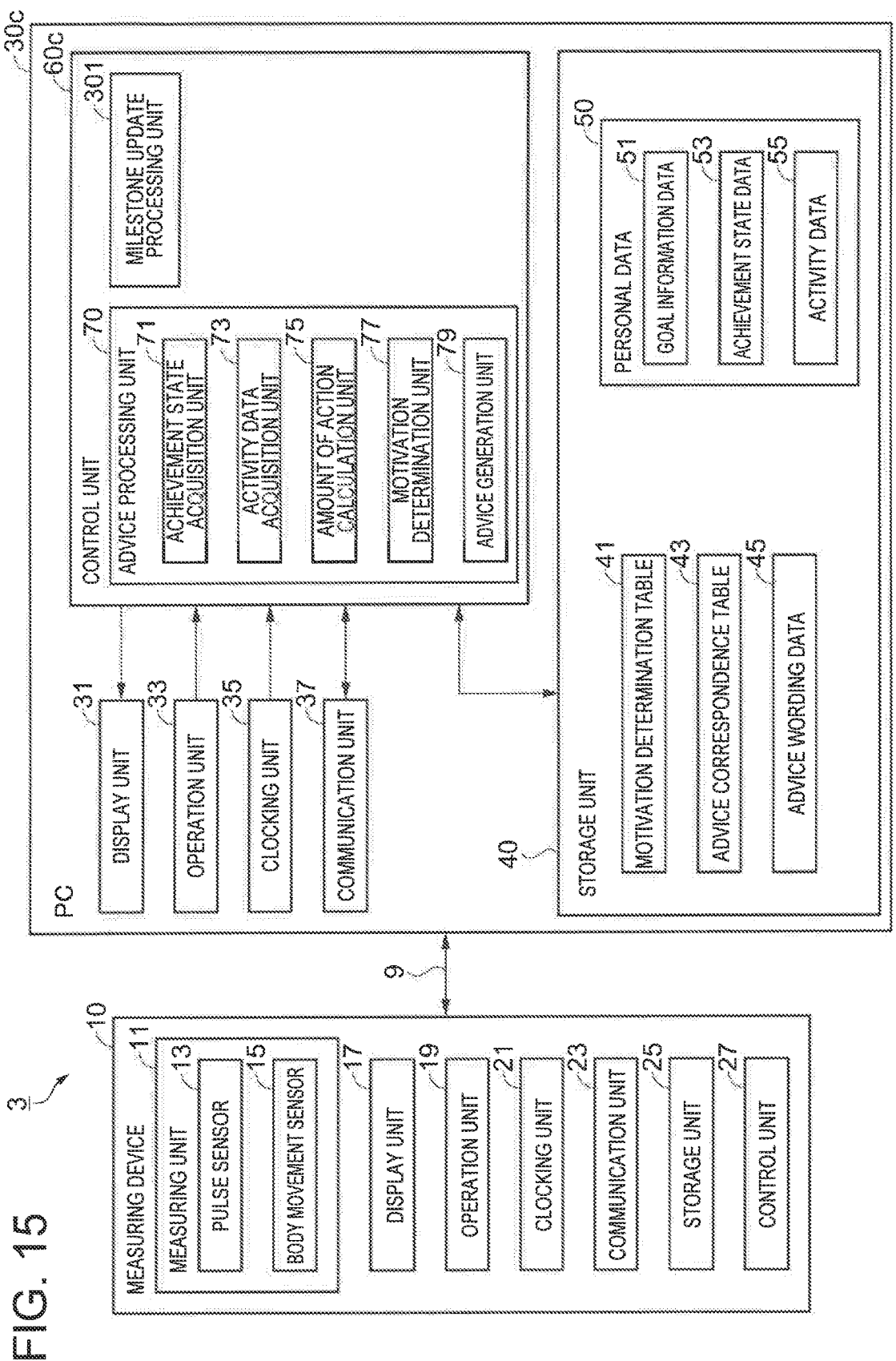
FIG. 15 is a block diagram showing a schematic configuration of an advice generation system according to Embodiment 3.
Figure 16:
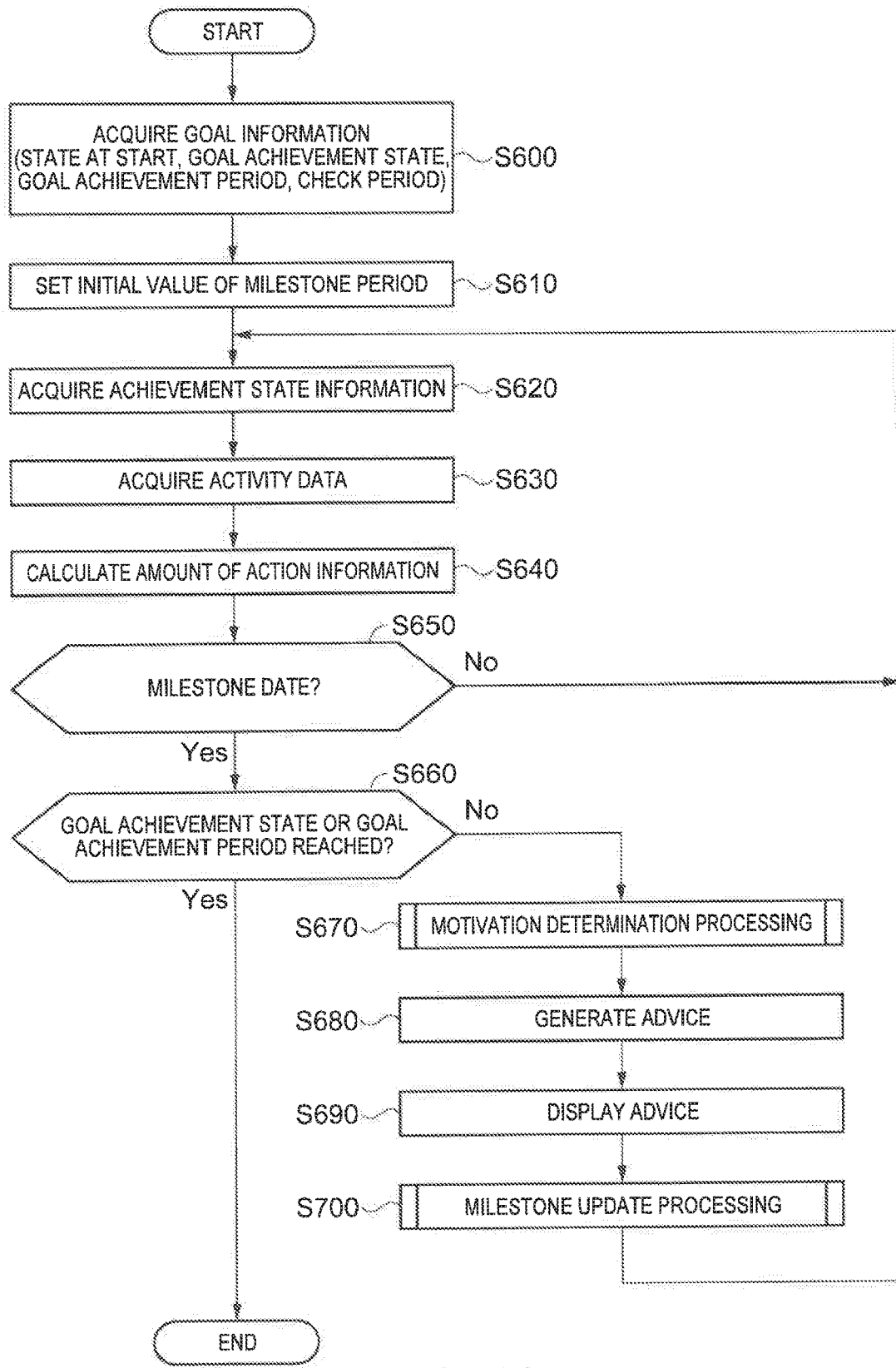
FIG. 16 is a flowchart showing a flow of milestone update processing.
Figure 17:
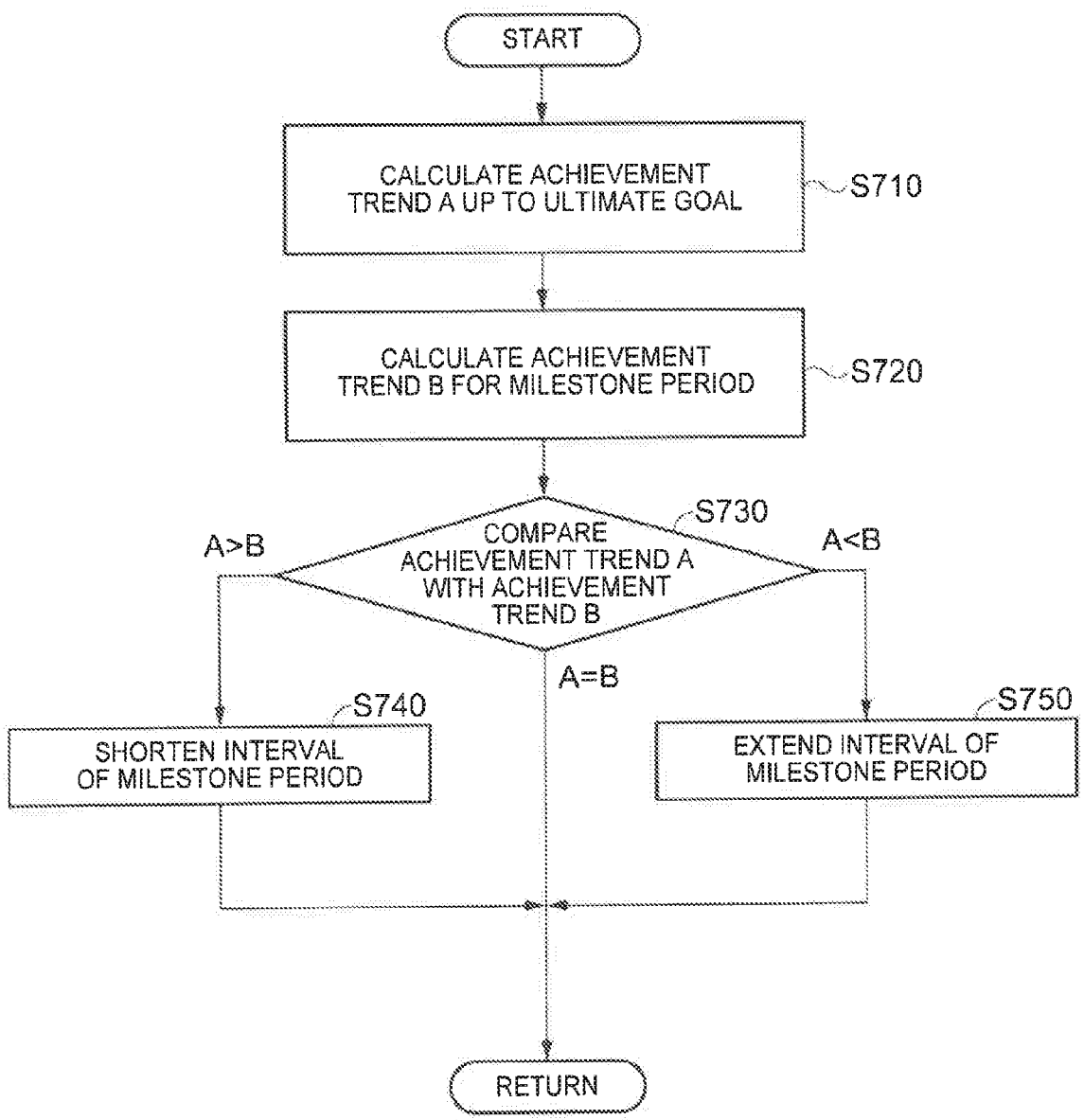
FIG. 17 is a flowchart showing a flow of milestone update processing.

Next, Embodiment 3 will be described using FIG. 15, FIG. 16, and FIG. 17. In the above embodiments, a regular check period is provided and information of the achievement state and the amount of action on the check date is acquired so as to generate advice. However, an advice generation system 3 according to Embodiment 3 is different in that the length of the check period is changed based on the result of determination on motivation. The other features are similar to those of the above embodiments. Also, components similar to those of the above embodiments are similarly applied to this embodiment. In FIG. 15 to FIG. 17, components similar to those of the above embodiments are denoted by reference signs similar to those in the illustrations explained in the above embodiments, and detailed explanation thereof is omitted.

In the description below, the check period is referred to as a milestone period, and the check date is referred to as a milestone date. On the milestone date, an intermediate goal is set in addition to checking the achievement state and the amount of action during the check period. The subject acts to achieve the intermediate goal during the milestone period, which is shorter than the period until the achievement of the goal, and repeats the achievement of the intermediate goal on the milestone date, thus ultimately achieving the goal. The milestone period corresponds to the predetermined period, similarly to the check period.

If the subject is allowed to feel that the achievement state of the intermediate goal on the milestone date is within reach, the state of achievability of the subject rises and the motivation can be maintained in a high state. Hereinafter, the advice generation system 3 which changes the milestone date based on the achievement state and the amount of action of the subject and thus can maintain the motivation of the subject in a high state, will be described below.

FIG. 15 is a block diagram showing a schematic configuration of the advice generation system 3 according to Embodiment 3. The advice generation system 3 is made up of a measuring device 10, a PC 30c and the like, and various data are transmitted and received between the two via wireless communication 9. The measuring device 10 and the wireless communication 9 are the same components as those of the foregoing embodiments. Hereinafter, different components from those of the foregoing embodiments will be described, mainly with respect to the PC 30c.

The PC 30c is configured with a control unit 60c and the like.

The control unit 60c is configured with a functional unit of a milestone update processing unit 301.

The milestone update processing unit 301 updates the milestone period. Specifically, the achievement trend up to the ultimate goal that is set at the time of setting the goal and the achievement trend up to the intermediate goal for the milestone period are compared, and if the achievement trend for the intermediate goal is above (more favorable than) the achievement trend for the ultimate goal, the interval of the subsequent milestone period is made longer. If the achievement trend for the intermediate goal is below (less favorable than) the achievement trend for the ultimate goal, the interval of the subsequent milestone period is made shorter. If the achievement trend for the ultimate goal and the achievement trend for the intermediate goal are substantially the same, the interval of the milestone period is not changed.

The milestone update processing unit 301 corresponds to the predetermined period change unit.

FIG. 16 is a flowchart showing the flow of milestone update processing. This flow is a flow of processing executed by the control unit 60c controlling each unit including the display unit 31, the operation unit 33, the clocking unit 35, the communication unit 37, and the storage unit 40 or the like. As this flow is executed, the functions of the functional units of the advice processing unit 70b and the milestone update processing unit 301 are implemented.

In Step S600, goal information is acquired. The goal information includes information such as the state at the start, the goal achievement state, the goal achievement period, and the check period. In Step S610, an initial value of the milestone period is set. As the milestone period, the check period acquired in Step S600 is set.

In Step S620, achievement state information is acquired. The achievement state data of the subject is acquired from the achievement state data 53 stored in the storage unit 40. In Step S630, activity data is acquired. The activity data of the subject is acquired from the activity data 55 stored in the storage unit 40. In Step S640, amount of action information is calculated. The amount of action is calculated from the activity data acquired in Step S630. The calculated amount of action is added up, thus calculating the cumulative value of the amount of action from the start of the action as well.

In Step S650, whether the milestone date has come or not is determined. If the milestone date has come (Step S650; Yes), the processing goes to Step S660. If the milestone date has not come (Step S650; No), the processing returns to Step S620 and Steps S620 to S640 are repeated.

In Step S660, whether the goal achievement state or the goal achievement period is reached or not is determined. If the achievement state acquired in Step S620 has reached the goal achievement state acquired in Step S600, or if the milestone date has reached the ending date of the goal achievement period (Step S660; Yes), this flow ends. If the goal achievement state is not reached and the ending date of the goal achievement period is not reached (Step S660; No), the processing goes to Step S670.

In Step S670, motivation determination processing is executed. In this step, the function of the motivation determination unit 77 is implemented and the state of motivation of the subject is determined. As the state of motivation, the states of achievability and urgency forming the motivation are determined. In Step S680, advice is generated. In Step S690, the advice is displayed.

In Step S700, milestone update processing is carried out. Specifically, using the goal information acquired in Step S600 and the achievement state information acquired in Step S620, the milestone period is changed and the next milestone date is decided. The decided milestone date is defined as a new milestone date, and the processing goes to Step S620.

As the milestone date is decided in Step S700 in this flow, the control unit 60c displays the next milestone date on the display unit 31 or the like. After that, the operation unit 33 is controlled to acquire, from the subject, information such as the achievement state for the intermediate goal toward the next milestone date.

Next, the milestone update processing will be explained.

FIG. 17 is a flowchart showing the flow of the milestone update processing. This flow is a flow showing the processing of Step S700 (FIG. 16) in detail.

In Step S710, an achievement trend A up to the ultimate goal is calculated. Specifically, the state at the start, the goal achievement state, and the goal achievement period are acquired from the goal information, and the achievement trend until the achievement of the ultimate goal is expressed by a numerical value. Specifically, the state at the start is subtracted from the goal achievement state, and the value obtained by dividing the result by the goal achievement period is calculated as the achievement trend A. For example, if the body weight is to be reduced by 30 kg in six months, 5 kg per month is calculated as the achievement trend A.

In Step S720, an achievement trend B for the milestone period is calculated. Specifically, referring to the achievement state acquired in Step S620, the first achievement state is subtracted from the last achievement state during the milestone period, and the value obtained by dividing the result by the milestone period is calculated as the achievement trend B. For example, if the milestone period is 2 months and 3 kg is lost during the milestone period, 1.5 kg per month is calculated as the achievement trend B.

Since the achievement trend A and the achievement trend B are compared with in a later step, the same unit needs to be used. In the above example, the weight lost per month is used as the unit.

In Step S730, the achievement trend A and the achievement trend B are compared. Specifically, the achievement trend A and the achievement trend B are compared, and if the achievement trend A is greater than the achievement trend B, the processing goes to Step S740. If the achievement trend A is smaller than the achievement trend B, the processing goes to Step S750. If the achievement trend A and the achievement trend B are substantially the same, the processing returns to Step S700. If the achievement trend A and the achievement trend B are substantially the same, a predetermined margin value may be provided, and if the difference between the achievement trend A and the achievement trend B is within a predetermined margin value range, it may be determined that these trends are the same. In this case, if the difference is above the range of the predetermined margin value range, the processing goes to Step S740. If the difference is below the predetermined margin value range, the processing goes to Step S750.

In Step S740, the interval of the milestone period is shortened. Specifically, the milestone period is set to a period that is three quarters, half or the like of the previous one. For example, the milestone period of one month is changed to three weeks or two weeks. After the milestone period is changed, the processing returns to Step S700.

In Step S750, the interval of the milestone period is extended. Specifically, the milestone period is set to a period that is twice, one and a half times or the like of the previous one. For example, the milestone period of one month is changed to two months or six weeks. After the milestone period is changed, the processing returns to Step S700.

In the flow of Steps S710 to S750, the condition that the milestone period is changed using the trend of the achievement state (achievement trend A and achievement trend B) is used. However, this method is not limiting and the milestone period may be changed using the amount of action information. In the case where the amount of action information is used, if the trend of change in the amount of action planned at the time of setting the goal is greater than the trend of change in the amount of action taken during the milestone period, the milestone period is set to be longer. On the contrary, if the trend of change in the amount of action taken during the milestone period is smaller, the milestone period is set to be shorter.

As described above, the advice generation system 3 according to the embodiment can achieve the following effects in addition to the effects of the foregoing embodiments.

According to the advice generation system 3, the milestone update processing unit 301 compares the achievement trend up to the ultimate goal set at the time of setting the goal and the achievement trend up to the intermediate goal for the milestone period. If, as the result of the comparison, achievement trend during the milestone period is below the achievement trend up to the ultimate goal and does not progress favorably, the subsequent milestone period is set to be shorter. Thus, for a subject whose achievement state is stagnating, there is a risk of lowered state of achievability, and in such a case, the subsequent milestone period is set to be shorter. As the milestone period is set to be shorter than before, the subject can reach the intermediate goal more easily and therefore the state of achievability is improved. As the state of achievement is improved, the motivation of the subject is increased and the achievement trend rises as well.

If the achievement trend for the milestone period is above the achievement trend up to the ultimate goal and progresses favorably, the subsequent milestone period is set to be longer. This has the effect of restoring the original milestone period from the shortened milestone period, if the achievement trend is improved favorably.

(Modification 1)

In the above Embodiment 3, the milestone update processing unit 301 compares the achievement trend up to the ultimate goal set at the time of setting the goal and the achievement trend up to the intermediate goal for the milestone period and updates the milestone period. However, this configuration is not limiting. The milestone period may be updated, using and comparing the states of achievability and urgency outputted from the motivation determination unit 77.

Specifically, if the achievability is determined as "low" by the motivation determination unit 77, or if the urgency is determined as "low", the subsequent milestone period is set to the shorter. Meanwhile, if the achievability is determined as "high" by the motivation determination unit 77, or if the urgency is determined as "high", the subsequent milestone period is set to be longer.

Using the result of the determination by the motivation determination unit 77, the milestone period can be set to be shorter for a subject whose motivation state is lowered, and the state of achievability can thus be improved.

(Modification 2)

This modification is described using FIG. 4, FIG. 11, and FIG. 15.

In the foregoing embodiments and modification, the advice generation system 1 (2, 3) is configured in such a way that the measuring device 10 and the PC 30 (30b, 30c) are connected together via the wireless communication 9. However, this configuration is not limiting and a configuration with the measuring device 10 only may be employed as well. In the measuring device 10 in such a configuration, the motivation determination table 41, the advice correspondence table 43, and the advice wording data 45 are stored in the storage unit 25 in advance, and the control unit 27 has a functional unit corresponding to the advice processing unit 70 (70*b*). With this configuration, in the measuring device 10 alone, advice generated based on pulse data and activity data measured by the measuring unit 11 is displayed on the display unit 17. The subject can receive advice to maintain and improve motivation, by wearing the measuring device 10 and acting accordingly.

The measuring device 10 in this modification corresponds to the advice generation device.

(Modification 3)

In the foregoing embodiments and modifications, the advice generation unit 79 (79*b*) generates advice wording for the subject. However, this configuration is not limiting. The advice generation unit 79 (79*b*) may generate icon data, animations, and graphs or the like. Motivation can be maintained and improved by expressions which the subject can easily understand.

Also, a configuration in which the result of the training status or the like of the subject may be shown in a graph or the like, may be included. Moreover, information of the training statuses of other subjects in the group to which the subject belongs may be processed by a statistical method and shown in a graph or the like. The subject can select information that is necessary for him/herself from various different kinds of information.

(Modification 4)

In the foregoing embodiments and modifications, the weight lost by the subject is used as an example of the achievement state information. However, depending on the set goal, the achievement state information may be, for example, a reduction in the time taken for running a predetermined distance such as 10 km or 20 km, or an athletic ability indicator such as a distance that the subject can run continuously. Also, the achievement state information may be a physical strength indicator such as maximum oxygen uptake, exercise duration until the maximum pulse rate is reached, the capacity of the lungs, and an indicator related to endurance.

REFERENCE SIGNS LIST

1, 2, 3 . . . advice generation system, 9 . . . wireless communication, 10 . . . measuring device, 11 . . . measuring unit, 13 . . . pulse sensor, 15 . . . body movement sensor, 17 . . . display unit, 19 . . . operation unit, 21 . . . clocking unit, 23 . . . communication unit, 25 . . . storage unit, 27 . . . control unit, 30, 30*b*, 30*c* . . . PC, 31 . . . display unit, 33 . . . operation unit, 35 . . . clocking unit, 37 . . . communication unit, 40, 40*b* . . . storage unit, 41 . . . motivation determination table, 43 . . . advice correspondence table, 45 . . . advice wording data, 50, 50*b* . . . personal data, 51 . . . goal information data, 53 . . . achievement state data, 55 . . . activity data, 60, 60*b*, 60*c* . . . control unit, 70, 70*b* . . . advice processing unit, 71 . . . achievement state acquisition unit, 73 . . . activity data acquisition unit, 75 . . . amount of action calculation unit, 77 . . . motivation determination unit, 79, 79*b* . . . advice generation unit, 201 . . . grouping unit, 210 . . . grouping table, 211 . . . group definition table, 213 . . . difficulty degree definition table, 215 . . . difficulty degree definition table, 217 . . . difficulty degree definition table, 230 . . . database, 231 . . . group information data, 240, 241 . . . advice, 301 . . . milestone update processing unit, 451, 453, 455, 461, 463, 465 . . . advice.

The invention claimed is:

1. An advice generation system which generates advice for achieving a goal, the system including:
   a sensor which measures an activity status of a subject and outputs activity data based on the activity status; and
   a processor that is programmed to function as:
   an achievement state acquisition unit which acquires achievement state information that is information of an achievement state with respect to a goal of the subject;
   an amount of action calculation unit which calculates amount of action information that is a cumulative amount of action taken by the subject based on the activity data acquired by the sensor;
   a motivation determination unit which determines motivation of the subject to achieve the goal based on the achievement state information and the amount of action information; and
   an advice generation unit which generates advice for the subject based on a result of the determination on the motivation,
   wherein the motivation determination unit determines the motivation based on a trend of change in the achievement state information and a trend of change in the amount of action information, determines levels of achievability of the subject and urgency of the subject, and determines that it is a first level of the achievability if the trend of change in the amount of action information is an ascending trend and the trend of change in the achievement state information is a trend of change that is approaching a goal achievement state.

2. The advice generation system according to claim 1, wherein the achievement state information and the amount of action information are acquired every predetermined period.

3. The advice generation system according to claim 1, wherein the motivation determination unit determines that the achievability is a second level of achievability that is lower than the first level of achievability, if the trend of change in the amount of action information is an ascending trend and the trend of change in the achievement state information is within a predetermined range of trend of change.

4. The advice generation system according to claim 3, wherein the motivation determination unit determines that the achievability is a third level of achievability that is lower than the second level of achievability, if the trend of change in the amount of action information is an ascending trend and the trend of change in the achievement state information is a trend of change that is far from a goal achievement state.

5. The advice generation system according to claim 1, wherein the motivation determination unit determines that it is a first level of urgency if the trend of change in the amount of action information is an ascending trend.

6. The advice generation system according to claim 5, wherein the motivation determination unit determines that the urgency is a second level of urgency that is lower than the first level of urgency, if the trend of change in the amount of action information is within a predetermined range of trend of change and the trend of change in the achievement state information is a trend of change that is far from a goal achievement state.

7. The advice generation system according to claim 6, wherein the motivation determination unit determines that the urgency is a third level of urgency that is lower than the second level of urgency, if the trend of change in the amount of action information is within a predetermined range of trend of change and the trend of change in the achievement state information is a trend of change that is approaching a goal achievement state.

8. The advice generation system according to claim 1, wherein the activity status includes a pulse rate of the subject and acceleration information based on a body movement of the subject, and the activity data includes at least one of pulse data calculated based on the pulse rate and acceleration data calculated based on the acceleration information.

9. The advice generation system according to claim 1, wherein the amount of action calculation unit calculates exercise intensity using at least one of the pulse data and the acceleration data of the subject, and calculates the amount of action based on the exercise intensity and a duration of the exercise intensity.

10. The advice generation system according to claim 1, wherein the amount of action calculation unit calculates calories burned, using at least one of the pulse data and the acceleration data of the subject, and calculates the amount of action based on the calories burned that are accumulated.

11. The advice generation system according to claim 1, wherein the achievement state information includes at least one of weight of the subject, a time taken for the subject to run a predetermined distance, a distance which the subject can run, and a physical strength indicator of the subject.

12. The advice generation system according to claim 11, wherein the physical strength indicator is a maximum oxygen uptake of the subject.

13. The advice generation system according to claim 1, further comprising:
a storage unit which acquires at least a goal, a period until the goal is achieved, and the activity data, of a plurality of subjects, and stores the achievement state information and the amount of action information acquired or calculated for each of the subjects; and
a grouping unit which groups the plurality of subjects based on the achievement state information and the amount of action information of the plurality of subjects stored in the storage unit,
wherein the advice generation unit generates advice for the subject, referring to the achievement state information and the amount of action information of the subject and another subject in the same group as the subject.

14. The advice generation system according to claim 1, further comprising:
a predetermined period change unit which changes an interval of a predetermined period based on a result of the determination on the motivation.

15. The advice generation system according to claim 14, wherein the predetermined period change unit changes the interval of the predetermined period to be longer if it is determined that the motivation is the first level of achievability.

16. The advice generation system according to claim 14, wherein the predetermined period change unit changes the interval of the predetermined period to be shorter if it is determined that the motivation is the second a second level of achievability or the third level of achievability.

17. An advice generation method for generating advice to achieve a goal, the method comprising:
sensing, using a sensor, an activity status of a subject and outputting activity data based on the activity status;
acquiring, using a processor, achievement state information that is information of an achievement state with respect to a goal of the subject;
calculating, using the processor, amount of action information that is a cumulative amount of action taken by the subject based on the activity data acquired by the sensing;
determining, using the processor, motivation of the subject to achieve the goal based on the achievement state information and the amount of action information;
determining, using the processor, the motivation based on a trend of change in the achievement state information and a trend of change in the amount of action information, levels of achievability of the subject and urgency of the subject, and a first level of the achievability if the trend of change in the amount of action information is an ascending trend and the trend of change in the achievement state information is a trend of change that is approaching a goal achievement state, and
generating, using the processor, advice for the subject based on a result of the determination on the motivation.

18. An advice generation device for generating advice to achieve a goal, the device comprising:
a sensor which measures an activity status of a subject and outputs activity data based on the activity status; and
a processor programmed to function as:
an achievement state acquisition unit which acquires achievement state information that is information of an achievement state with respect to a goal of the subject;
an amount of action calculation unit which calculates amount of action information that is a cumulative amount of action taken by the subject based on the activity data acquired by the sensor;
a motivation determination unit which determines motivation of the subject to achieve the goal based on the achievement state information and the amount of action information; and
an advice generation unit which generates advice for the subject based on a result of the determination on the motivation,
wherein the motivation determination unit determines the motivation based on a trend of change in the achievement state information and a trend of change in the amount of action information, determines levels of achievability of the subject and urgency of the subject, and determines that it is a first level of the achievability if the trend of change in the amount of action information is an ascending trend and the trend of change in the achievement state information is a trend of change that is approaching a goal achievement state.

* * * * *